US008868616B1

(12) United States Patent
Otto et al.

(10) Patent No.: US 8,868,616 B1
(45) Date of Patent: Oct. 21, 2014

(54) EVENT DATA MONITORING SYSTEMS AND METHODS

(75) Inventors: Chris A. Otto, Huntsville, AL (US);
Chirag D. Patel, Chicago, IL (US);
Hugh A. Hartwig, Madison, AL (US);
Corey L. Sanders, Madison, AL (US);
Xiao Fang Chen, Huntsville, AL (US)

(73) Assignee: Integrity Tracking, LLC, Boca Raton, FL (US)

( * ) Notice: Subject to any disclaimer, the term of this patent is extended or adjusted under 35 U.S.C. 154(b) by 0 days.

(21) Appl. No.: 13/544,988

(22) Filed: Jul. 9, 2012

Related U.S. Application Data

(60) Provisional application No. 61/505,387, filed on Jul. 7, 2011.

(51) Int. Cl.
*G06F 17/30* (2006.01)

(52) U.S. Cl.
CPC .................. *G06F 17/3053* (2013.01)
USPC ........... 707/802; 707/803; 707/804; 707/805; 378/19; 455/404.1; 455/404.2; 379/37; 379/38; 379/39; 379/40

(58) Field of Classification Search
CPC ................................................ G06F 17/30053
USPC .......... 707/802–805, 702; 378/19; 455/404.2, 455/404.1; 379/37–40
See application file for complete search history.

(56) References Cited

U.S. PATENT DOCUMENTS

| 5,221,088 A | 6/1993 | McTeigue et al. |
| 5,372,365 A | 12/1994 | McTeigue et al. |
| 5,400,246 A | 3/1995 | Wilson et al. |
| 5,440,135 A | 8/1995 | Shonka |
| 5,959,529 A | 9/1999 | Kail, IV |
| 6,160,478 A | 12/2000 | Jacobsen et al. |
| 6,198,394 B1 | 3/2001 | Jacobsen et al. |
| 6,609,076 B2 | 8/2003 | Schuh et al. |
| 6,809,012 B2 | 10/2004 | Yamazaki et al. |
| 6,894,509 B2 | 5/2005 | Johnson et al. |

(Continued)

FOREIGN PATENT DOCUMENTS

WO WO2006/064397 A2 6/2006

OTHER PUBLICATIONS

Jovanov, Emil et al., A Wireless Body Area Network of Intelligent Motion Sensors for Computer Assisted Physical Rehabilitation, Journal of NeuroEngineering and Rehabilitation, Rochester, MN, Mar. 2005.

(Continued)

*Primary Examiner* — Frantz Coby
(74) *Attorney, Agent, or Firm* — Ann I. Dennen; Lanier Ford Shaver & Payne P.C.

(57) ABSTRACT

A personal monitoring system of the present disclosure has a network and a sensing device. The sensing device has a network interface for coupling the sensing device to the network and is coupled to a user for sensing raw data at a discrete time related to the user. Additionally, the system has logic that associates a timestamp with the raw data at the discrete time and stores the raw data as raw history data indicative of a plurality of raw data from discrete times. Further, the logic determines, based upon the raw history data, whether an event has occurred.

41 Claims, 10 Drawing Sheets

(56) References Cited

U.S. PATENT DOCUMENTS

| | | | |
|---|---|---|---|
| 7,004,910 B2 | 2/2006 | Lindsey | |
| 7,145,461 B2 | 12/2006 | Lehrman et al. | |
| 7,211,053 B2 | 5/2007 | Marmaropoulos et al. | |
| 7,515,043 B2 | 4/2009 | Welch et al. | |
| 7,515,044 B2 | 4/2009 | Welch et al. | |
| 7,558,622 B2 | 7/2009 | Tran | |
| 7,646,845 B2 * | 1/2010 | Lecomte et al. | 378/19 |
| 7,717,858 B2 | 5/2010 | Massad | |
| 7,742,816 B2 | 6/2010 | Masoud et al. | |
| 7,843,325 B2 | 11/2010 | Otto | |
| 8,007,436 B2 | 8/2011 | Katayama | |
| 8,073,707 B2 | 12/2011 | Teller et al. | |
| 8,190,753 B2 * | 5/2012 | Nguyen | 709/229 |
| 8,206,325 B1 | 6/2012 | Najafi et al. | |
| 8,401,514 B2 * | 3/2013 | Ebdon et al. | 455/404.1 |
| 2004/0027246 A1 | 2/2004 | Aguglia | |
| 2004/0059205 A1 | 3/2004 | Carlson et al. | |
| 2004/0199056 A1 | 10/2004 | Husemann et al. | |
| 2005/0107723 A1 | 5/2005 | Wehman et al. | |
| 2007/0038268 A1 | 2/2007 | Weinberg et al. | |
| 2007/0063850 A1 | 3/2007 | Devaul et al. | |
| 2007/0209669 A1 | 9/2007 | Derchak | |
| 2007/0219059 A1 | 9/2007 | Schwartz et al. | |
| 2007/0250286 A1 | 10/2007 | Duncan et al. | |
| 2008/0001735 A1 | 1/2008 | Tran | |
| 2008/0052399 A1 * | 2/2008 | Nguyen | 709/227 |
| 2010/0075629 A1 * | 3/2010 | Anderson | 455/404.2 |
| 2012/0302197 A1 * | 11/2012 | Koontz et al. | 455/404.2 |

OTHER PUBLICATIONS

Kouvatsos, D. D. et al, Performance Issues in a Secure Health Monitoring Wireless Sensor Network, University of Bradford, Bradford, UK.

Christian, Andrew et al., Gathering Motion Data Using Featherweight Sensors and TCP/IP over 802.15.4, Cambridge Research Laboratory, IEEE International Symposium on Wearable Computing, Workshop on On-Body Sensing, Osaka, JP, Oct. 2005.

Lo, Benny P. L. et al., Body Sensor Network—A Wireless Sensor Platform for Pervasive Healthcare Monitoring, Imperial College, London, UK.

Jovanov, Emil, Wireless Technology and System Integration in Body Are Networks for m-Health Applications, University of Alabama in Huntsville, Huntsville, AL.

* cited by examiner

EVENT DATA MONITORING SYSTEMS AND METHODS

CROSS REFERENCE TO RELATED APPLICATIONS

This application claims priority to Provisional Patent Application U.S. Ser. No. 61/505,387, entitled "Field Instrumentation Methods for Human Fall Detection System" and filed on Jul. 7, 2011, which is fully incorporated herein by reference.

BACKGROUND

Oftentimes, elderly individuals who are at risk of falling or have medical conditions needing fast emergency response use personal emergency response systems to request assistance. Traditionally these systems are manually activated using a button, sometimes referred to as a "panic button" or more recently incorporating automatic fall detection capability as described in U.S. patent application Ser. No. 12/192,855, entitled, which is incorporated herein by reference in its entirety.

Typically, emergency response devices consist of a wearable pendant with a button that a user can actuate in order to signal to a responder that he/she is in need of help. Such systems are typically characterized by a gateway computing device that resides in the home. The gateway computing device provides connectivity to a service provider (i.e., a responder) via a hard wired phone line connection via a public switched telephone network (PSTN).

Some emergency response devices may include an automatic fall detection capability. Typically, such capability detects falls without a user pressing the button. Additionally, some emergency response devices monitor physiological characteristics. Further, some are mobile systems that are unconstrained by the user's proximity to his/her residence or the device's access to a phone line.

Typically, such devices rely on complex central monitoring units that use complex signal processing in order to effectively manage data generated by the devices. In these types of devices, the device performs event detection and feature extraction, and typically do not have the capacity to communicate such relevant information for example for post-mortem analysis of reported issues and ongoing improvements of the device.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout the several views.

DETAILED DESCRIPTION

The present disclosure relates to an event monitoring system that enables a user employing the system to obtain help during an emergency. The personal emergency response system comprises a monitor that is worn and/or in close proximity to the user during times when the user is at risk for needing assistance if an emergency event occurs, e.g., when the user is alone at his/her residence.

During use, the monitor senses and records user characteristic data indicative of physiological, motion, and location characteristics related to the user. The monitor transmits the user characteristic data to a computing device over a network, e.g., a cellular network, to a computing device.

The data received by the computing device is stored and is available for real-time or subsequent access. The computing device may notify a caregiver of the received characteristic data or notify the caregiver of events that occur as evidenced by the characteristic data received. Based upon the information received by the caregiver, the caregiver may contact the user. In one embodiment, the caregiver may contact via a network the monitoring device via a number specifically assigned to the monitoring device similar to a mobile phone number. In one embodiment, in response to a call, the monitor automatically creates a network connection with the caregiver and activates a speakerphone through which the caregiver can speak with the user. In addition, the caregiver can contact additional individuals designated as emergency contacts and/or request an emergency response team to the user. In one embodiment, the monitor records data of the user's location (e.g., global positioning system data) which the computing device stores and which can be used to locate the user if the user's whereabouts are unknown.

Additionally, the monitor is equipped to detect if the user falls. In this regard, the monitor analog signals and such signals are manipulated by a computing device on the edge of a network. Further, the present disclosure describes a system that enables algorithms employed to manipulate such signals to improve over time without capturing the entirety of sampled data.

Figure 1:
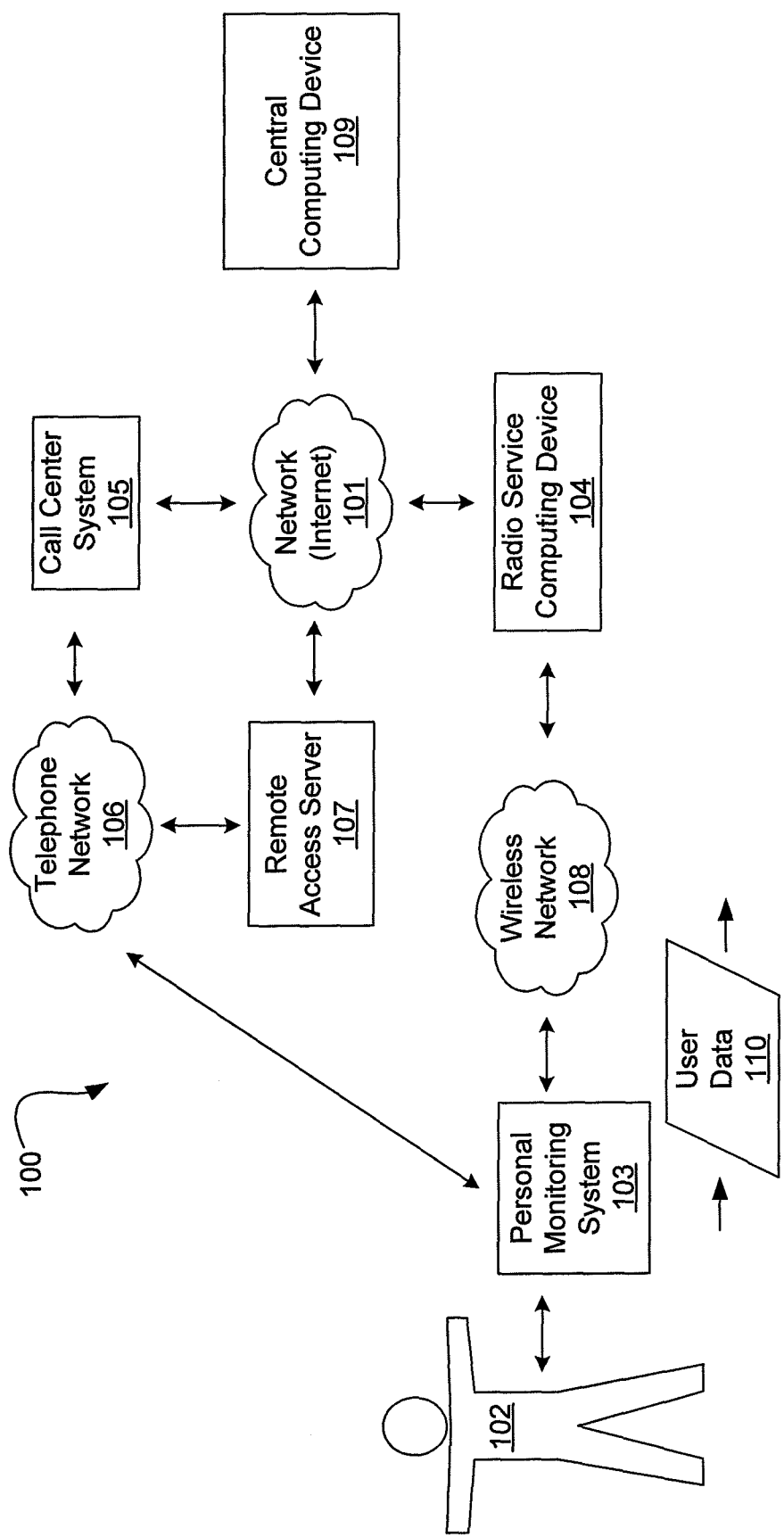
FIG. 1 is a block diagram of an exemplary event monitoring system in accordance with an embodiment of the present disclosure.

FIG. 1 is a block diagram of an exemplary personal monitoring system 100 in accordance with an embodiment of the present disclosure. The system 100 comprises a monitoring device 103 that is worn on or kept in close proximity to a user 102. In addition, the system 100 comprises a radio service computing device 104 and a central computing device 109 that communicate via a network 101. Further, the system 100 comprises a call center system 105 that is accessible via the interne 101 and a remote access server 107, each of which is accessible by the central computing device 109. The call center 105 and the remote access server 107 each may communicate with the personal monitoring system 103 via the telephone network 106.

Figure 2:
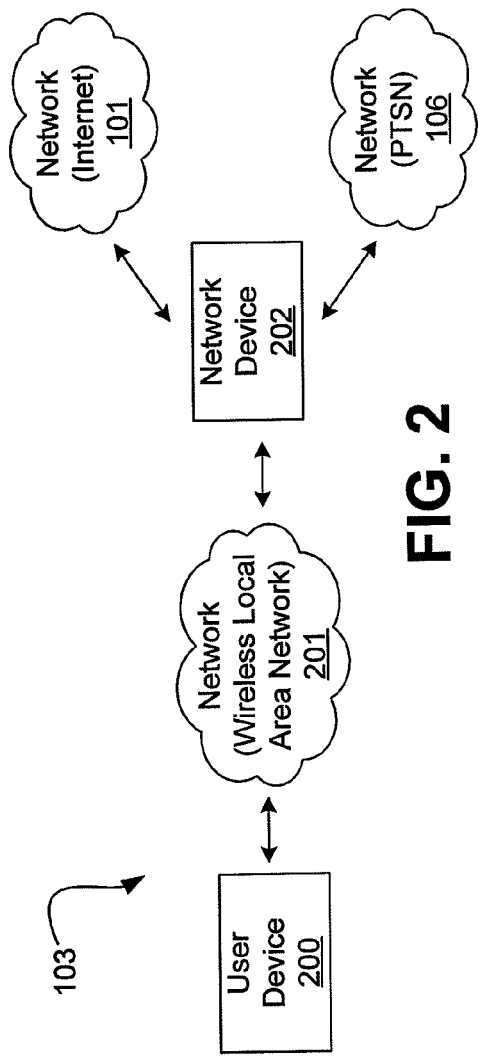
FIG. 2 is a block diagram of an exemplary event monitoring system such as is depicted in FIG. 1.

The personal monitoring system 103, described further with reference to FIG. 2, automatically monitors the user. In this regard, the personal monitoring system 103 collects the characteristic data related to the user, which may include but is not limited to physiological, motion, and location data, hereinafter collectively referred to as "user data."

The personal monitoring system 103 transmits collected user data 110 to a radio service computing device 104 via a wireless network 108. The radio service computing device 104 transmits the user data to the central computing device 109 via the network 101.

The central computing device 109 stores the user data 110 received via the network 101. In addition to storing the user data 110, the central computing device 109 analyzes the user data 110 received and determines if an event has occurred, e.g., the user 102 has fallen, and sends a notification to the call center system 104 via the network 101. If such a notification is made, the call center system 105 may automatically create a connection, e.g., a voice connection, to the personal monitoring system 103 via the telephone network 106 or a caregiver may be monitoring the call center system 105 and manually place a phone call to the personal monitoring system 103 via the telephone network 106. In addition, the central computing device 109 may connect to the personal monitoring system 103 through the remote access server 107 via the telephone network 106.

In one embodiment, the wireless network 108 is a mobile device network. The mobile device network may be, for example, a cellular network, that communicates via radio waves. In one embodiment, the user device 200 may communicate over a public switched telephone network (PSTN). In such a configuration, a user of a mobile device (not shown) may connect to any other phone (mobile or land line) in the world. Other configurations may be employed in other embodiments. For example, the personal monitoring system 103 may communicate with the central computing device 109 via satellite technology.

In one embodiment, the network 101 is the Internet. However, other types of networks may be used in other embodiments to implement the system 100. In this regard, any type of packet-switched networks may be used that connect the radio service computing device 104 to the central computing device 109.

In one embodiment, the telephone network 106 is a public switched telephone network (PSTN). The PSTN is a collection of circuit-switched telephone networks that may employ various technologies for communicating, e.g., telephone lines, fiber optic lines, microwave, cellular towers, and/or satellites. Note that in one embodiment the wireless network 108 may be a part of the telephone network 106. However, for illustration of the system 100 of the present disclosure, no such linkage or inclusion is shown in FIG. 1. Note that the system 100 enables bidirectional data traffic, i.e., from the personal monitoring system 103 to the central computing device 109. A system for monitoring health data is described in U.S. patent application Ser. No. 12/686,342, entitled *Human Health Monitoring Systems and Methods* (the '342 application), which is incorporated herein by reference in its entirety.

FIG. 2 is a block diagram illustrating an exemplary personal monitoring system 103. The personal monitoring system 103 comprises a user device 200 and a networking device 202 that communicate via a network 201, e.g., a wireless local area network (LAN). The network device 202 may be configured to connect to the telephone network 106 (e.g., PSTN) and/or the network 101 (e.g., Internet). The network device 202 is described further with reference to FIG. 4.

The user device 200 may be any type of device that is worn by the user 102 (FIG. 1). The user device 200 may be any type of device that senses, stores, and transmits user data 110 and enables the user 102 to be contacted (or to contact) a caregiver for assistance. An exemplary user device may include, but is not limited to a mobile phone (including a smart phone), belt clip, chest strap, pendant, watch, and/or arm band, for example.

In one embodiment, the user device 200 comprises a mechanism (not shown) that enables the user 102 to quickly and easily request help. Such a mechanism may include, but is not limited to a manual push button that when selected automatically dials a caregiver (or someone who can contact the caregiver for the user 102).

In one embodiment, the user device 200 comprises a battery to provide power for the device. In one embodiment, the user device 200 comprises a global positioning system (GPS) for obtaining location data (not shown) describing the precise location of the user 102. In one embodiment, the user device 200 comprises mobile network interface equipment (such as a global system for mobile communication (GSM) or code division multiple access (CDMA) radio) that enables the user device 200 to transmit user data 110 (including location information, such as latitude and longitude data) via the wireless network 108 and provide 2-way communication between the user 102 and the call center system 105 (FIG. 1) via the network 106. In one embodiment, the device 200 further comprises a sensor (e.g., an accelerometer or barometric pressure sensor) that performs motion analysis and fall detection so that the user data 110 may contain data indicative of motion data related to the user. Such a device/system is described in U.S. patent application Ser. No. 12/192,855 entitled Wearable Health Monitoring Device and Methods for Fall Detection, U.S. patent application Ser. No. 12/192,830 entitled Wearable Health Monitoring Device and Methods for Step Detection (the '830 application) and U.S. patent application Ser. No. 12/192,855 entitled Wearable Health Monitoring Device and Methods for Fall Detection (the '855 application), which are incorporated herein by reference in their entirety.

Additionally, the user device 200 may be configured to detect whether the user 102 has fallen. If a fall occurs, the user device 200 may establish a telephone connection via the network 106 with the call center computing device 105. The device may also utilize an accelerometer to provide activity measurement and steps as described in the '830 application; an ECG circuit to monitor heart rate; a thermometer to read temperature; and a barometric pressure sensor for measuring elevation. Such a user device 200 is described in the '830 application, the '855 application, and U.S. patent application Ser. No. 12/972,039 entitled Wireless Sensor Network System and Method (the '039 application), which are incorporated herein by reference in their entirety.

In one embodiment, the network 201 is a wireless local area network (WLAN). In such an embodiment, the network 201 links the user device 200 with the networking device 202 via a wireless communication method, such as, for example Bluetooth® or Zigbee®.

Figure 4:
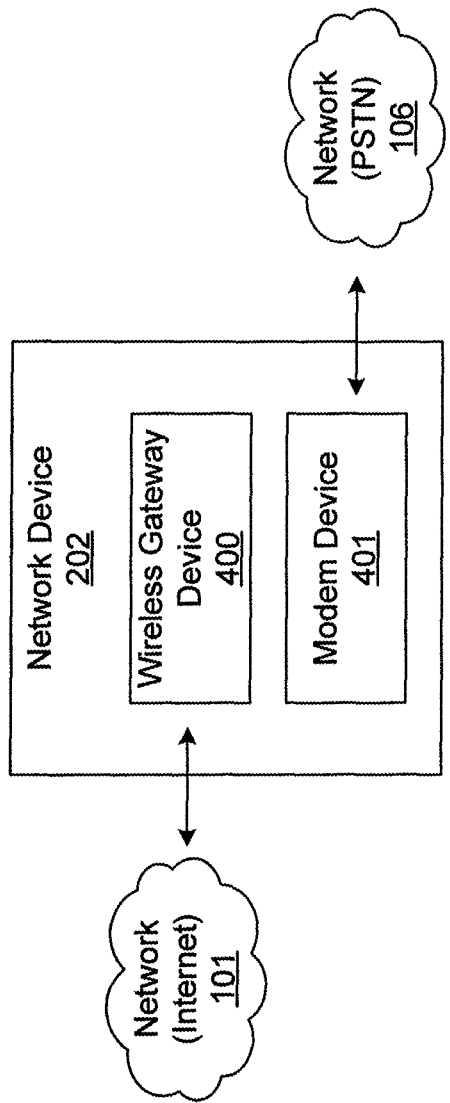
FIG. 4 is a block diagram of a network device such as is depicted in FIG. 2.

With reference to FIG. 4, in one embodiment, the networking device 202 comprises a wireless gateway device 400 and a modem 401. The wireless gateway device 400 is a computing device that routes packets from the network 201 to the network 101 (e.g., the Internet). The wireless gateway device 400 may serve as a wireless access point to the network 101, a router, and/or a firewall. The modem 401 may be any type of digital subscriber line (DSL) modem or cable modem that connects the WLAN 201 to the network 101.

Thus, with reference to FIG. 1, the user device 200 may connect to and communicate with the central computing device 109 through the wireless network 108 and the network 101 using radio communication methods and the radio service computing device 104. In addition, the user device 200 may communicate with the central computing device 109 through the network 201 and the network 101 using radio communication methods and the network device 202. Furthermore, the user device 200 may contact or be contacted by the call center computing device 105. Such contact may be established, for example, when the call center computing device 105 establishes a connection with a telephone number assigned to the user device 200 (e.g., a cell phone or mobile number).

Figure 3:
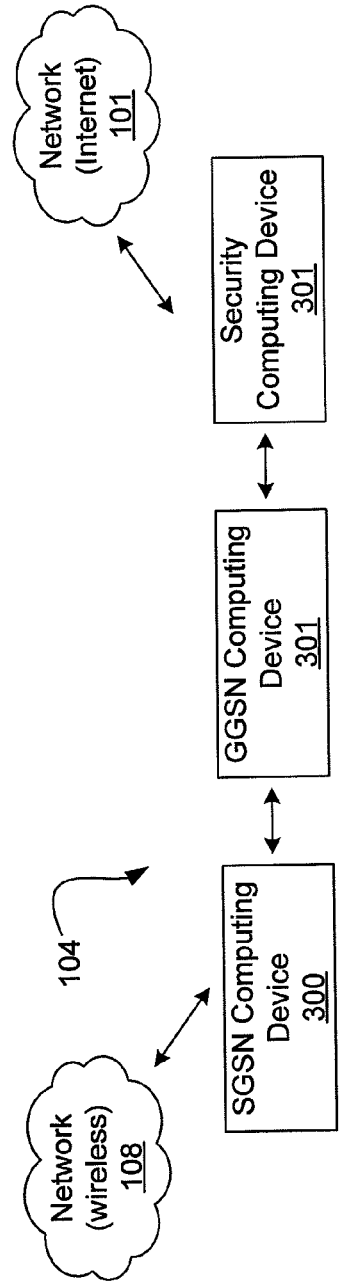
FIG. 3 is a block diagram of an exemplary radio service computing device such as is depicted in FIG. 1.

FIG. 3 depicts an exemplary embodiment of a radio service computing device 104. The exemplary radio service computing device 104 is a general packet radio service (GPRS) radio service computing device 104 that comprises a serving GPRS support node (SGSN) computing device 300, a gateway GPRS service node (GGSN) computing device 301, and a security computing device 301, e.g., a firewall. Note that in such an embodiment, the GPRS is a packet mobile data service that enables communication on the global system for mobile communications (GSM). In this regard, the GPRS computing device 104 allows mobile networks, e.g., 2G, 3G, 4G, WCDMA, etc., to transmit internet protocol (IP) packets to the network 101 (FIG. 1).

During operation, the SGSN computing device 300 receives data user data 110 (e.g., in the form of packets) from the user device 200 via the network 108, translates the user data 110 received, and performs authentication of the user 102. The GGSN computing device 301 converts the user data 110 into the appropriate packet data protocol (PDP) format (e.g., IP or X.25) and sends them out on the corresponding network 101. Further, data may be sent to the user device 200 (FIG. 2) via the network 108. In this regard, data packets (not shown) received from the network 101 addressed to the user device 200 are translated to GSM standard data packets.

Note that the radio service computing device 104 is depicted and described as an exemplary embodiment. Other technologies, protocols, and/or types of systems may be used to connect the user device 200 employing mobile communication methods to the network 101, e.g., the Internet.

Figure 5:
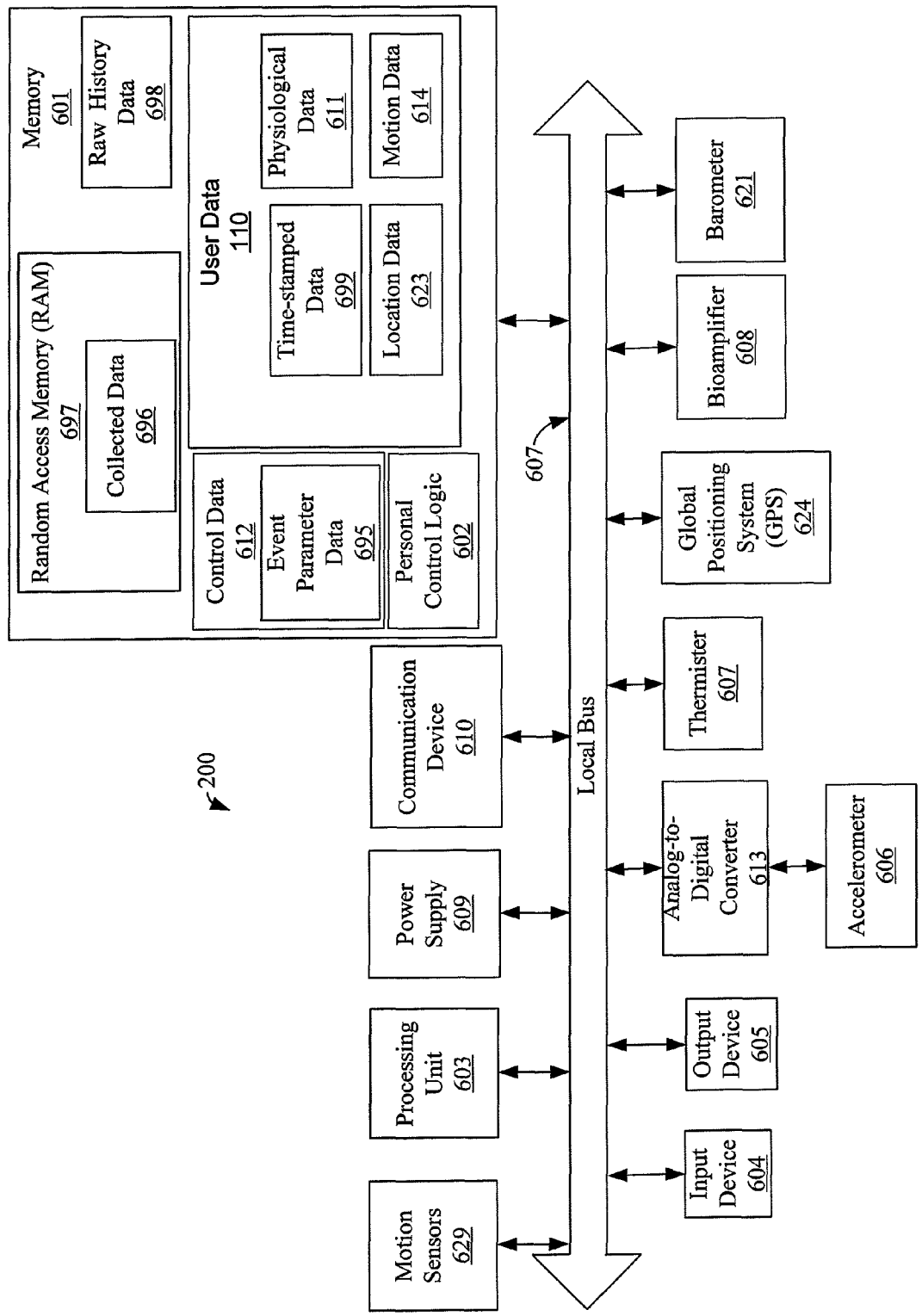
FIG. 5 is a block diagram of an exemplary user device such as is depicted in FIG. 2.

FIG. 5 is a block diagram depicting an exemplary user device 200 of the present disclosure. The exemplary user device 200 comprises a processor 603, an output device 605, an input device 604, a communication device 610, and a power supply 609. In addition, the exemplary user device 200 comprises a thermistor 607, one or more bioamplifiers 608, barometer 612, and other motion sensors 629. Each of these components communicates over local interface 607, which can include one or more buses. Furthermore, the user device 200 comprises an accelerometer 606 and an analog-to-digital converter (ADC) 613. Further, the user device 200 comprises a global positioning system (GPS) 624.

The other motion sensors 629 may include additional accelerometers or inertia sensors, for example. Any type of motion sensor known in the art or future-developed may be used to detect motion of the user 102 (FIG. 1).

User device 200 further comprises raw history data 698, personal control logic 602, user data 110, and control data 612. The user data 110 may include physiological data 611, motion data 614, times-tamped data 699, and location data 623. Personal control logic 602 can be software, hardware, or a combination thereof. In the exemplary user device 200 shown in FIG. 6, personal control logic 602, is shown as software stored in memory 601. Memory 601 may be of any type of memory known in the art, including, but not limited to random access memory (RAM), read-only memory (ROM), flash memory, and the like. Note that a portion of memory 601 is shown as being random access memory 697 for storing collected data 696 for subsequent use for a limited period of time.

Figure 6:
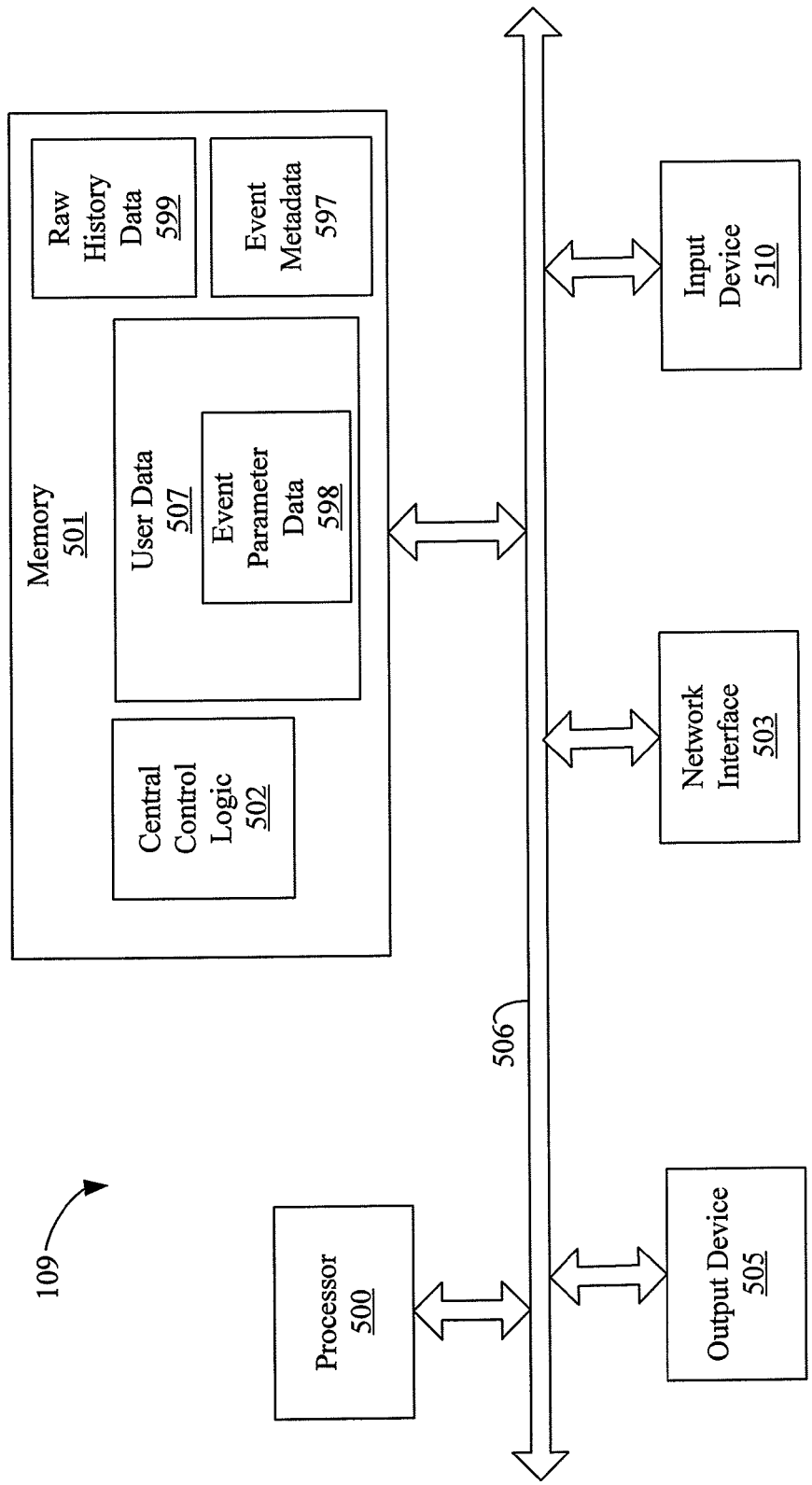
FIG. 6 is a block diagram of an exemplary central computing device such as is depicted in FIG. 1.

As noted hereinabove, personal control logic 602, user data 610, control data 612, and raw history data 698 are shown in FIG. 6 as software stored in memory 601. When stored in memory 601, personal control logic 602, user data 610, control data 612, and raw history data 698 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium Processor 603 may be a digital signal processor (DSP) or other type of circuitry configured to run the personal control logic 602 by processing and executing the instructions of the personal control logic 602. By way of example, the processor 603 may be an Advanced Reduced Instruction Set Computer (RISC) Machine (ARM) 7, ARM 9, Intel® PXA901, Intel 80386, Freescale® HCx08, Freescale® HCx11, Texas Instruments® MSP430, or a digital signal processor (DSP) architecture. The processor 603 communicates to and drives the other elements within the device via the local interface 607.

The communication device 610 may be, for example, a low-powered radio device, e.g., a radio semiconductor, radio frequency antenna antenna); a wired communication device such a RS232, USB, or Ethernet; or other wireless communication device, such as a magnetic communications scheme or infrared scheme; or any type of communication device, which communicatively couples the user device 200 central computing device 109. In this regard, the communication device 610 communicatively couples the device 200 with another network or device, for example a network controller, access gateway, or directly to a cellular network.

The sensor logic 804 communicates bi-directionally through the communications network device 805 with an intermediary gateway or directly to the central computing device 109 (via the network).

In an embodiment having a data-receiving unit 302, physiological data 611 and motion data 614 can be relayed in a real-time manner, a periodic manner, an "as they occur" fashion, or some combination of the three. For example, a serious condition such as an individual falling could be relayed to the central monitoring device 305 (FIG. 3).

In one embodiment, the bioamplifier 608 is a device that interfaces with the electrodes 200. Thus, the bioamplifier 608 gathers, amplifies, filters and conditions the signal integrity of human physiological activity for use by the personal control logic 602. The signals (not shown) collected by the bioamplifier 608 from the electrodes 200 relate to the nervous system of the user 301 (FIG. 3). In one embodiment, the signals collected are stored as the physiological data 611, and are used by the personal control logic 602.

The output device 605 is a device for communicating information to the user 102 (FIG. 1). The output device 605 may be, for example, an LED that indicates that power is on. In addition, the output device 605 may be a speaker that emits a sound upon the occurrence of a particular event, e.g., when the battery needs to be charged or upon activation.

Physiological data 611 includes data obtained from the one or more sensors, e.g., the thermistor 607 or the bioamplifier 608. Hence, the physiological data 611 comprises data indicative of physiological aspects of the user 301 (FIG. 3). Examples of physiological data 611 include data indicative of ECG readings, heartbeat readings, temperature readings, or the like.

Motion data 614 includes data obtained from the accelerometer 606. Hence, the motion data 614 comprises data indicative of movement of the user. In the 3-axis accelerometer embodiment, the motion data 614 includes data indicative of the user 301 in an X-direction, Y-direction, and the Z-direction.

Location data 623 is any data that describes the location of the user 102 that is wearing the user device 200. In this regard, the location data 623 may be any data indicative of reading obtained from the GPS 624.

The time-stamped data 699, which is described further herein, comprises data indicative of raw data captured from one or more sensing devices, e.g., motion sensors 629, accelerometer 606, thermister 607, bioamplifier 608, or barometer 621, for example (collectively "the sensors"). In addition to the captured raw data, the time-stamped data 699 stores data for each raw data entry indicative of the time that the raw data was captured from the sensors.

The raw history data 698 comprises a plurality of sets of raw data captured from the sensors. In one embodiment, each set of raw data captures comprises data indicative of one or more readings taken from one or more of the sensors at a discrete time, i.e., a discrete point in time.

The control data 612 is data indicative of various settings and/or parameters that may be used by the personal control logic 602 to operate the user device 200. The control data comprises event parameter data 695. The event parameter data 695 comprises data indicative of thresholds that may be indicated for which the personal control logic 602 compares data obtained from the sensors to determine if an event has occurred.

The input device 604 enables the user 102 to enter data into the user device 200. In the exemplary user device 200, the input device 604 may be a push button. When the push button is selected, the user device 200 generates a message which is sent over the networks 108 and 101 to the central computing device 109 as an emergency event. Other input devices may be used in other embodiments. For example, the input device 604 may be a keyboard or a touch screen for performing particular operations on the user device 200.

In one embodiment, the input device 604 is a microphone (not shown), and an exemplary output device 605 is a speaker (not shown), as described hereinabove. In such an embodiment, the speaker and the microphone enable the user 102 to be in communication with the call center system 105 or the caregiver (not shown). In such an example, the user device 200 detects an event, such as, for example, a fall or a negative change in the user's physiological condition based upon physiological data 611. The central computing device 109 receives user data 110 that includes the physiological data 611 and transmits an alert to the call center system 105 or the caregiver. The call center system 105 or caregiver may then contact the user 102 over the network 106 via the microphone/speaker input/output arrangement.

The thermistor 607 is conductively coupled to a metal contact (not shown). The thermistor 607 is a device that measures a skin temperature of the user 102 where the thermistor 607 is in contact with the metal contact, which is in contact with the skin of the user 102. In one embodiment, the thermistor 607 is a thermocouple (not shown).

In one embodiment, the accelerometer 606 is a 3-axis accelerometer for monitoring motion. The accelerometer 606 may be a direct current ("DC") response or a non-DC response accelerometer. In one embodiment, the accelerometer 606 is a microelectromechanical ("MEMS") piezoresistive technology sensor (not shown), however other types of accelerometers known in the art or future-developed may be used in other embodiments of the user device 200.

In one embodiment, the accelerometer 606 measures acceleration due to gravity and physical movement and transmits the raw analog signals to the ADC 613. The ADC 613 translates the received analog into digital data indicative of the received analog signals (not shown). The ADC 613 provides the digital data indicative of the analog signals to the personal control logic 602, which can store the digital data as motion data 614. The personal control logic 602 then calculates and stores additional motion data 614 including activity-induced energy expenditure (AEE) and/or orientation, based upon the motion data 614. In addition, the personal control logic 602 can use the motion data 614 to detect a fall, detect steps made by the user 301, and categorize activity performed by the user 301. The accelerometer 606 may be a single (or dual) axis accelerometer arranged to create a three-axis orthogonal coordinate system, as depicted in FIG. 3 as X, Y, and Z axes.

During extraction of the physiological data 611 and motion data 614, the personal control logic 602 reacts quickly to changes in real-time and also reduces the data stream, thereby maximizing the storage capabilities of memory 601. Reducing the data stream may refer to techniques for averaging the data, or inspecting the real-time stream for certain feature extraction. One such technique is described in U.S. patent application Ser. No. 11/972,335 entitled Wireless Sensor Network Context Data Delivery System and Method.

The barometer 621 is any device that is capable of determining barometric pressure. Thus, the barometer 621 obtains a barometric pressure measurement, e.g., air pressure measurement, and the personal control logic 602 can calculate the user's location in reference to the user's height above sea level. Such calculated height may be stored in the user data The GPS 624 is any system that communicates with a satellite (not shown), for example, to obtain location data 623 related to where the user 102 is located. In this regard, the GPS 624 may obtain longitude and latitude data that identifies the user's location.

In one embodiment of the system 100 (FIG. 1), the user device 200 may tend to use a considerable amount of power from the power supply 609 (FIG. 6), e.g., a battery. One method of efficiently utilizing power resources is described in the '335 application.

In one embodiment of the system 100, the personal control logic 602 throttles GPS location queries performed by the GPS 624 (FIG. 6). In this regard, the personal control logic 602 obtains past motion data 614 obtained from a particular sensor, e.g., the accelerometer 606 and performs a first order approximation on the motion data 614 to determine if there is an indicated change in the user's location. In this regard, the personal control logic 602 calculates an estimated measure of the user's estimated positional change. Further, the system personal control logic 602 stores data indicative of the last known location obtained from GPS 624 as location data 623 and samples another motion-based sensor 629 (FIG. 6) (e.g., a lower power consuming sensor) to estimate detected steps or expended energy. The personal control logic 602 then calculates an estimate of the user's activity in a given time frame. For example, a threshold may be determined such as if the user has taken less than 100 steps in the previous hour then send the last known location. Obtaining the last known location avoids using a power intensive resource such as the GPS receiver to obtain a precise location when it is estimated that the user's location has not changed appreciably. If the user has not expended enough motion or steps to change their location appreciably, then checking the GPS 624 (or other location based sensor) would expend unnecessary battery power. Instead the GPS 624 remains inactive or idle. The '830 application described a method for determining the number of steps a user has taken during a given period of time.

In another embodiment, the user device 200 may not send location data 623 to the central computing device 109 until the user device personal control logic 602 determines that the user's location has changed appreciably, e.g., a threshold of steps have been taken that indicates that location data 623 needs to be updated on the central computing device 109. In such an embodiment, the personal control logic 602 may continue to transmit other user data 110 to the central computing device 109 in a periodic fashion so that the central computing device 109 may discern the scenario when the user has not changed location and the scenario when the device is not operational or out of range from a communication infrastructure.

In one embodiment, the user device 200 detects whether the user 102 has fallen or taken steps as described in the '855 application or taken steps. In such an embodiment, the personal control logic 602 may control periodic measurements taken from the accelerometer. In this regard, the personal control logic 602 may not take measurements from the accelerometer 602 until a threshold of change is determined and the acceleration ceases after a period of time.

In another embodiment, the user device 200 may extend the battery life by utilizing piezoelectric MEMS devices (not shown) that harvest kinetic energy. Such devices typically take advantage of Faraday's Law and rely on natural vibrations to move a tiny electromagnetic generator (not shown). Modern piezoelectric kinetic scavenging MEMS devices can generate several hundred microwatts of power. While perhaps not sufficient to power the user device 200 completely, the power generated may be used to augment the power subsystem and be channeled to storage in the power supply 609, e.g., the battery. Or similarly, the power generated may be used to supplement power so as to minimize draw on the power supply 609. This method would depend on the relative activity level of the user but could be used to delay charging or extend the usable life of the device between charges.

In one embodiment, the user device personal control logic 602 determines whether the user device 200 is being worn by the user 102 to ensure efficacy of user data 110 transmitted. In this regard, data indicating whether the user device 200 is being worn when the user data 110 is obtained may be used to aid the caregivers in helping the user 102 and provide statistics regarding problems leading to the user 102 not wearing the user device 200.

In one embodiment, the user device 200 may comprise a mechanical trigger (not shown), e.g., an actuator or switch. The mechanical trigger may be toggled when the user 102 attaches or removes the user device 200. Data indicative of such attachment and/or removal may be transmitted with the user data 110.

In another embodiment, the user device 200 may comprise a touch less proximity sensor that reacts to changes in magnetic or RF field (examples are Hall Effect sensors or an RF-capacitive human body proximity sensor which may detect a change in capacitance as a result of near proximity to a human body). In another embodiment, the user device 200 may comprise a thermal measurement instrument, e.g., thermistor 607. Since bodies naturally emit heat, detection of that heat using a thermistor, infrared receiver, or other temperature reading device can indicate that the user device 200 is being worn.

In another embodiment, the personal control logic 602 may record stationary movement, e.g., breathing, heart beating, scratching, muscle movement and spasms, etc. The personal control logic 602 may determine if the user device 200 is being worn based on such user data 110 indicative of the stationary movements In one embodiment, the control logic 200 may roam a geographical area in which the user is present to obtain data relating to available networks. In such an embodiment, the control logic 200 may select another network for use in delivering data to the central computing device 109. When the user device 200 is not transmitting across the network 108, the user device 200 may use other networks and transmission methods to deliver user data 110 and ensure security, such as a REST POST interface as seen in the '335 application.

For example, the user device 200 may be in close proximity to a wireless network, such as an 802.11g network. The user device 200 detects the wireless network, connects to the located network automatically, and transmits data through the wireless network instead of through the network 108. Additionally, at a home or facility where there is a wireless personal area network (WPAN), such as ZigBee® or 6LoPAN, the user device 200 may transmit measurements to these WPANs and communicate with an existing emergency response system in place at other locations.

In one embodiment, the WPANs may not allow user data 110 in particular protocols generated by the user device 200. In such an embodiment, the user device 200 retains the user data 110 that the user device 200 was unable to transmit and transmits the retained user data 110 at a later time. Notably, the user device 200 may connect to multiple different WPANs at a given time. When no network is found by the personal control logic 602, user data 110 is stored in nonvolatile memory for later transmission. Such a system is described in the '342 application.

As described hereinabove, the personal control logic 602 stores location data 623 periodically that the personal control logic 602 sends with user data 110 to the central computing device 109. Such location data 623 contained in the user data 110 may be used to track the location of the user 102. In this regard, a caregiver may have an itinerary of the user 102 that the user 102 is intended to follow over a period of time. Such location data 623 can be used by the caregiver to ensure that the user 102 follows the itinerary. Note that in one embodiment, the personal control logic 602 disables its location tracking capability so that it is unable to track the user's location.

In one embodiment, the user device 200 transmits location data 623 in the user data 110 periodically or on-demand. If the user device 200 transmits location data 623 in the user data 110 periodically (e.g., at set intervals of time), the central control logic 502 generates user data 110 indicative of the user's location history.

If the user device 200 transmits location data 623 on demand, the central control logic 502 transmits a notification to the user device 200, such as with short message service (SMS) or through an acknowledgement message. Upon receipt, the user device 200 queries the GPS 624 and transmits user data 110 containing the location data 623 to the central computing device 109.

Additionally, the user device 200 is configured to collect "raw data" from the various sensors, e.g., accelerometer 606, GPS 624, bioamplifier 608, barometer 621, and other sensors 629 (hereinafter referred to collectively as "the sensors"), and manages events that may occur related to the user. Note that the term "raw data" refers to data, e.g., numbers, characters, and/or symbols that have a particular meaning, that have not yet been processed by a computing device or other processor. Raw data may be stored in a file in memory. In the present disclosure, the raw data is the specific data received from the sensors and it is simply stored in the format received. Because it has not been processed by the computer in any way, it is considered to be "raw data."

In this regard, the personal control logic 602 assesses a timestamp for each reading obtained by the sensors and stores time-stamped data 699 in memory 601. Such time-stamped data 699 comprises the data indicative of each reading obtained by each sensor and a timestamp for each reading obtained.

In one embodiment, the personal control logic 602 stores raw data from the sensors as raw history data 698. The personal control logic 602 may then perform calculations and analysis on the raw data history buffer 698 to determine if an event has occurred. As an example, the personal control logic 602 may determine a certain fall or a possible fall. A possible fall may be an event of interest that has satisfied some subset a fall algorithm, but not enough to satisfy an actual fall. Because it may be determined later that the event in question was a fall, the personal control logic 602 stores the raw history data 698 that may then be analyzed at a later time. The personal control logic 602 may further determine that the possible fall may can be classified as a lower severity as described further herein.

Figure 8:
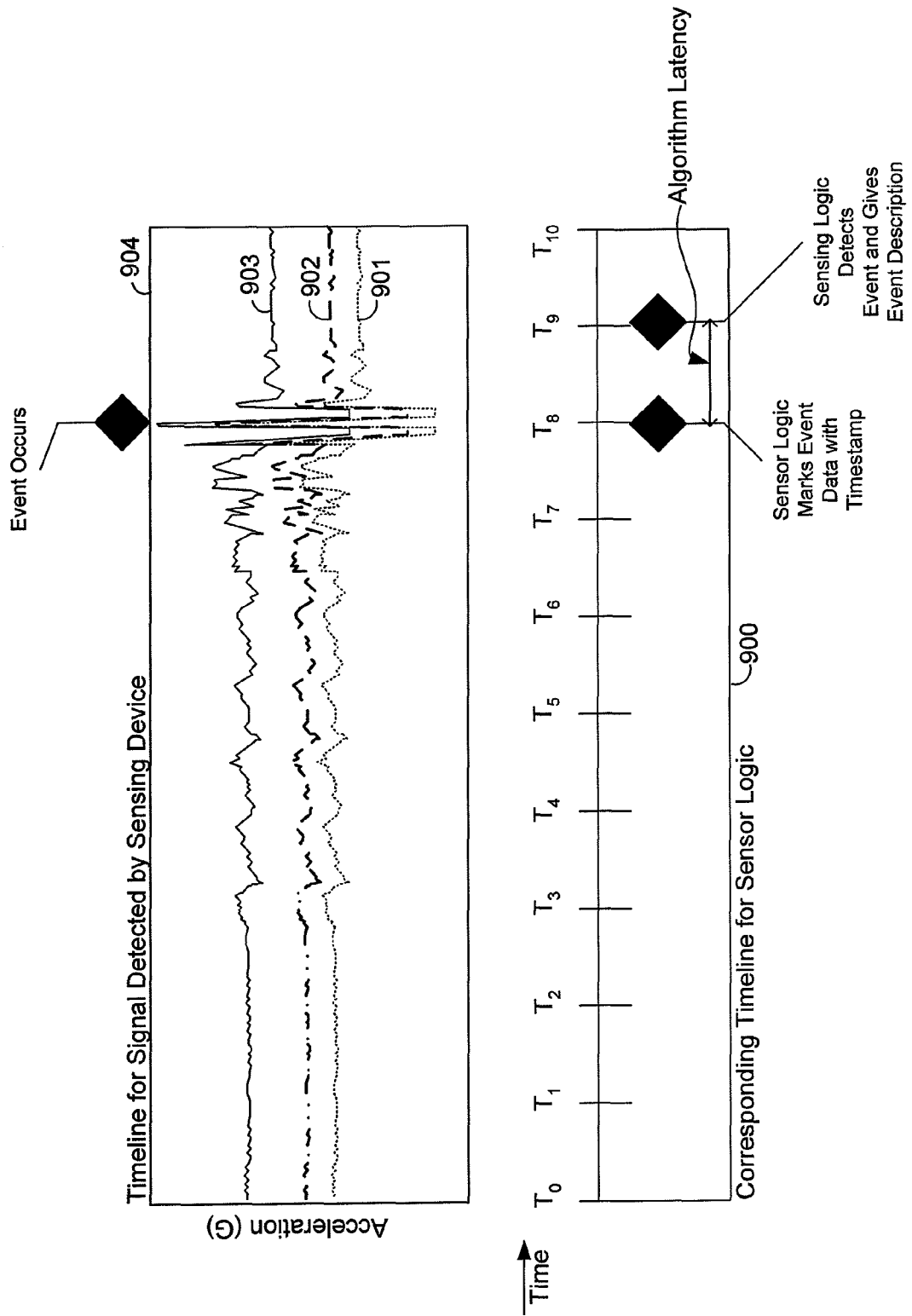
FIG. 8 is graph depicting an event timeline and corresponding control logic event identification.

To illustrate, FIG. 8 depicts a timeline 904 for three axis accelerometer data (Ax, Ay, and Az) obtained from accelerometer 606 and a corresponding timeline 900 for the personal control logic 602 when performing fall detection. The timeline 904 depicts signals and control logic events over time $T_0$ to $T_{10}$. In this regard, graph line 903 depicts data obtained in the x-direction, graph line 902 depicts data obtained in the y-direction, and graph line 901 depicts data obtained in the z-direction.

As shown in the timeline 904, the lines 901-903 experience a change at time $T_8$. Based on a network time reference, the control logic 902 assesses an "original timestamp" to the event occurrence at $T_8$ when the event is detected. Thus, the original timestamp is correlated with the actual event because the original timestamp is accessed prior to the personal control logic 602 performing any analysis of the data obtained from the accelerometer 606. Thus, the original timestamp is independent of latency in utilizing any on-sensor resource (memory or other), and independent of network transmission time which can vary widely depending on the organization of the network and the variability inherent in heterogeneous networks.

Notably, at time $T_9$ the personal control logic 602 completes processing of the event and categorizes the event as an event of interest, e.g., a fall. However, at time $T_9$ latency has occurred and the actual time of the event differs from the time when the control logic 606 completes its analysis and categorization of the data obtained. In this regard, the original timestamp provided by the personal control logic 602 is independent of latency that may occur due to processing of the data obtained. Thus, in one embodiment, the control logic 606 assesses timestamps to each data point sampled from the sensors. When the control logic 606 determines the occurrence of an event, the original timestamp (assessed on the original data point) can be used as the timestamp for the occurrence of the event.

As illustrated in the example of FIG. 8, the area of interest lies from approximately $T_2$ to $T_{10}$. In general, some time interval before and after the event would be of interest and is not limited to the number displayed. Thus, the control logic 606 stores raw history data 698 for the data indicative of the signals Ax, Ay, and Az during a period of time prior to the event and for s subsequent period of time after the event. In the example provided, the raw history data 698 comprises data for the six time intervals prior to event occurrence and for two intervals following the event. By storing at least seven time intervals of collected samples in the raw history data 698, the personal control logic 602 captures data that includes data samples indicative of signals occurring prior to an area of interest, and then continue including new samples of interest occurring following the event. Thus, the control logic 606 can begin a raw data capture record with data samples from the raw history data 698 and continue appending data collected within the area of interest through time interval $T_{10}$ as demonstrated in this example.

The personal control logic 602 may use a variety of triggers in order to begin storing raw history data 698. In this regard, the control logic may receive data indicating a fall, a possible fall, or the user may manually indicate to the personal control logic 602 to begin capturing raw history data 698. If a fall event is detected by the personal control logic 602, the personal control logic 602 recovers recent raw measurements to be reported for analysis. In manual activation, an actuator, e.g., a push button, causes the personal control logic 602 to begin storing raw data in the raw history data 698.

In one embodiment, the personal control logic 602 may be activated for raw data capture discretely and raw data capture may be enabled or disabled via remote management commands. In this embodiment, the control data 612 may store data indicative of a particular configuration, e.g., raw data capture on or off. Other data may also be stored related to the raw data capture such as, for example, the number of samples to collect and under what conditions to begin raw data capture.

In such an embodiment, the central computing device 109 may transmit a command to the user device 200 and change the control data 612 to change the raw data capture features, e.g., turn it on, off, or change the number of samples captured.

In one embodiment, the personal control logic 602 collects data periodically in real-time from the sensors and stores the collected data 696 in system random access memory (RAM) 697 and/or non-volatile memory by means of data structure such as a circular queue or buffer memory constituting the raw history data 698. U.S. patent application Ser. No. 12/911, 498, entitled Wireless Sensor Network Context Data Delivery System and Method ('498 application) and U.S. patent application Ser. No. 11/972,335, entitled Wireless Sensor Network Context Data Delivery System and Method ('335 application) describe techniques for storing hierarchical memory structures which may include various costs (on-chip RAM, off-chip RAM, on-chip non-volatile memory, and off-chip non-volatile memory), both of which are incorporated herein by reference in their entirety.

When the personal control logic 602 is triggered so that it is operating in raw data collection mode, a data structure (containing data samples before the event), may be transmitted to the central computing device 109 either directly or through the network device 202 (e.g., a gateway device).

Once the data structure fills with data after the event, the personal control logic 602 may transmit additional data. If at the time of the personal control logic 602 is unable to transmit the raw history data 698, the raw history data 698 is stored as collected data 696 in Nonvolatile or RAM 697 such as described in the '498 application.

FIG. 6 depicts an exemplary embodiment of the central computing device 109. The central computing device 109 comprises central control logic 502 for generally controlling the operation and functionality of the central computing device 109. In the exemplary embodiment shown by FIG. 6, control logic 502 is implemented in software and stored in memory 501. In other embodiments, the control logic 502 may be implemented in firmware, hardware, or any combination of software, firmware, and/or hardware.

The central computing device 109 further comprises user data 507 stored in memory 501. The user data 507 stores user data 110 and other data related to the user 102, including any data determined based upon the user data 110 received from the user device 200.

The exemplary embodiment of the central computing device 109 depicted by FIG. 6 includes a processor 500, which comprises processing hardware for executing instructions stored in memory 501. The processor 500 communicates to and drives the other elements within the central computing device 109 via a local interface 506, which can include at least one bus.

Furthermore, the central computing device 109 comprises a network interface 503. The network interface 503 may be any type of communication device that communicatively couples the central computing device 109 with the network 101 (FIG. 1) and the call center computing device 105 and the remote access a server 107.

In addition, the central computing device 109 comprises an output device 505. The output device 505 may be any type of device known in the art or future-developed that provides data to a user (or caregiver) using the central computing device 109. As a mere example, the display device 305 may be a liquid crystal display (LCD).

Furthermore, the central computing device 109 comprises an input device 510. The input device 510 may be, for example, a keyboard.

The central control logic 502 receives user data 110, which includes data indicative of physiological data 611 (FIG. 5), motion data 614 (FIG. 5), and location data 623 (FIG. 5), and stores the user data 110 as user data 507. An exemplary central computing device 109 is described in U.S. patent application Ser. No. 12/686,352, entitled Wireless Sensor Network System and Method for Using Same (the '352 application), and U.S. patent application Ser. No. 12/686,296, entitled Human Health Monitoring Graphical User Interface Systems and Methods (the '296 application), each of which is incorporated herein by reference in its entirety.

During operation, the central control logic 502 analyzes the user data 507. In this regard, the central control logic 502 may take action if the data 507 indicates the necessity. As an example, the central control logic 502 may notify the call center system 105 via the network 101 that an event (e.g., a fall) has occurred that needs immediate attention, based upon the user data 507.

In one embodiment, the central control logic 502 displays to the output device 605 a graphical user interface (GUI) (not shown) that enables a user of the central computing device 109 to view user data 507 and/or take action based upon the viewed user data 507. One such GUI is described in the '296 application. In one embodiment, the central control logic 502 displays a dashboard (not shown) where a user can view user data 507 indicative of past or present information about the user 102. Such a display may be in the form of a chronological list (not shown), which is a timeline of events for which user data 507 has been received and/or generated.

The GUI may further display location information contained in the user data 507 to the user of the central computing device 109. In this regard, the central control logic 502 may calculate a person's location, described further herein, based upon user data 507 indicative of latitude and longitude information. In particular, the user data 506 is periodically updated and/or modified with additional information available provided by the user device 200.

As described hereinabove, the central computing device 109 may receive raw history data 698 (FIG. 5) from the user device 200. In one embodiment, the network device 202, e.g., a gateway device, transmits the data to the central computing device 109. In such an example, the network device 202 is configured to organize the raw history data 698 into a discrete raw data capture record (RDCR) comprised of data indicative of a plurality of samples from the sensors and organized by sensor. For example, an RDCR may include data captured from an accelerometer with three separate axes of measurements as well as a barometric pressure sensor. In this example, the network device 202 organizes the raw history data into four discrete channels where the first three channels represent independent axes of the accelerometer and the fourth channel represents the barometric pressure sensor. The RDCR may also include an identifier for the device sending the capture data, a time stamp where the measurements were taken, a sequence number, and optionally a length field. The timestamp is used to mark precisely the time of the event that triggered the data collection.

Figure 9:
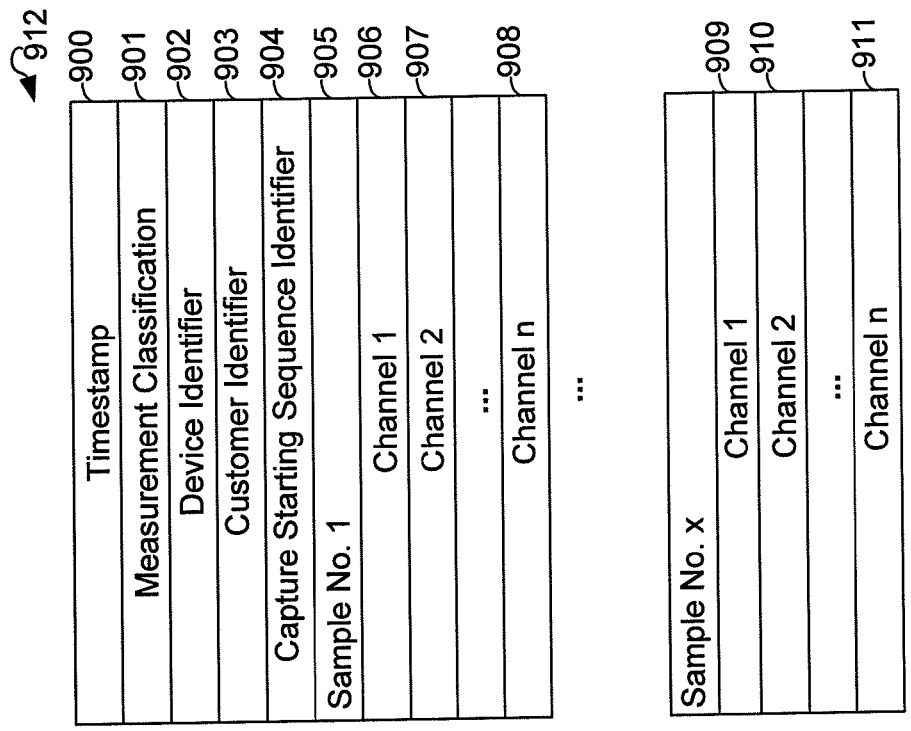
FIG. 9 is an exemplary raw history data packet used in the system depicted in FIG. 1.

In one embodiment, the central computing device 109 may comprise data indicative of a sampling rate for the sensors. In the case where the central computing device 109 comprises data indicative of the sensor sampling rate on user device 200, the entries in the raw history data 599 may each have the same timestamp. An exemplary data packet (for the RDCR) format is illustrated in FIG. 9. A data packet 912 is depicted. The data packet 912 comprises a timestamp entry 900, a measurement classification entry 901, a device identifier 902, a customer identifier 903, and a capture starting sequence identifier 904. In addition, the data captured may be transmitted in the packet comprising a sample number 905 and data obtained and transmitted in the channels 1, 2, n indicated by entries 906, 907, and 908. Additional samples may be transmitted as well as indicated in entries 909-911.

The data packet 912 is delivered to the central computing device 109. The data packet 912 may be delivered using any number of formats including a REST POST of XML. One such example is shown below:

<oscope_msgs>
  <timestamp>Mon Dec 25 15:52:55-0600 2007</timestamp>
  <oscope_msg>
    <channel_num>1</channel_num>
    <point><seq>19849</seq><data>2566</data></point>
    <point><seq>19850</seq><data>2324</data></point>
    <timestamp>Thu Nov 19 19:07:20 UTC 2009</timestamp>
    <user_id>276</user_id>
  </oscope_msg>
  <oscope_msg>
    <channel_num>2</channel_num>
    <point><seq>19849</seq><data>2219</data></point>
    <point><seq>19850</seq><data>2206</data></point>

```
<timestamp>Thu Nov 19 19:07:20 UTC 2009</timestamp>
<user_id>276</user_id>
</oscope_msg>
<oscope_msg>
    <channel_num>3</channel_num>
    <point><seq>19849</seq><data>2219</data></point>
    <point><seq>19850</seq><data>2206</data></point>
    <timestamp>Thu Nov 19 19:07:20 UTC 2009</timestamp>
    <user_id>276</user_id>
</oscope_msg>
<oscope_msg>
    <channel_num>4</channel_num>
    <point><seq>19849</seq><data>2219</data></point>
    <point><seq>19850</seq><data>2206</data></point>
    <timestamp>Thu Nov 19 19:07:20 UTC 2009</timestamp>
    <user_id>276</user_id>
</oscope_msg>
</oscope_msgs>
```

The sequence number identifier 904 comprises data indicative of a sequence number of a first item in an array of samples. In one embodiment, the central control logic 502 implies a sequence number for each data point indicated by the entries 906-911, after the first entry sample number 905. The implied sequence number may be a number indicative of the sequence identifier 904 incremented or the sequence identifier before it incremented. The sequence number identifier 904 resolves the order in which the samples were collected, yielding proper ordering with respect to time. The channel numbers indicted in entries 906-911 are used to discern one axis from another; or more generally to discern data collected from different sensors. A length field may also be integrated into the data packet 912 per channel to indicate how many data points for a given channel. Note that a length channel may not be needed if the total number of data points is fixed per the sensors.

Figure 10:
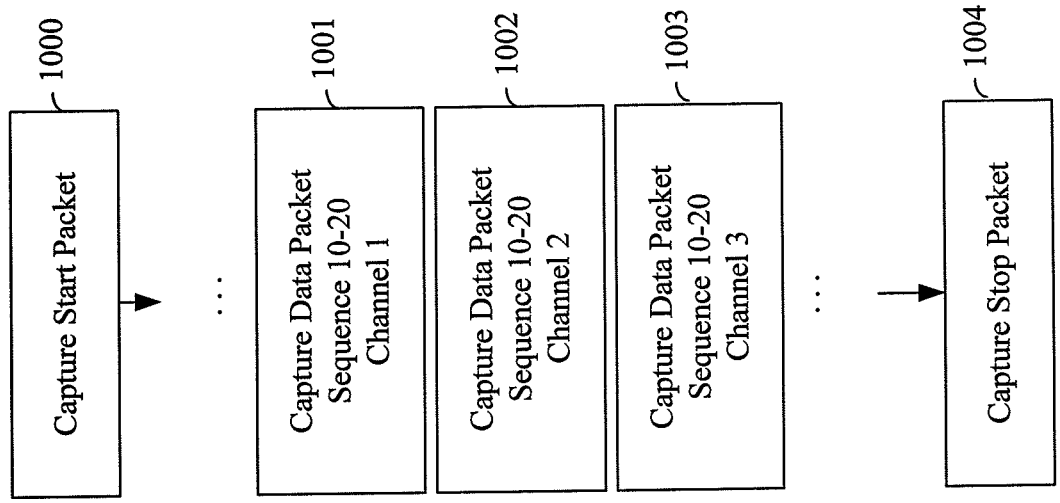
FIG. 10 is a flowchart of exemplary architecture and functionality of the user device such as is depicted in FIG. 2.

When transmitting the record over the network, the network device 202 may segment the RDCR file into a number of smaller data packets (not shown) for transfer. In such a scenario, a standard file transfer protocol may be used or, alternatively, an application specific RDCR transfer protocol may used. By way of example an RDCR start message can be used to signify a start of record transfer and an RDCR stop message may be used to signify stop of transfer. The start record message may signify the identifier of the device (or user) sending the capture data, and the time of the collection reported in each of the data point packets. An exemplary message transmission sequence is illustrated in FIG. 10. The message transmission sequence may be a capture start packet as indicated by block 1000. An example of a RDCR start packet is show below:

```
<oscope_start_msg>
    <capture_reason>Actual Fall </capture_reason>
    <timestamp>Mon Dec 25 15:52:55-0600 2007</timestamp>
    <user_id>276</user_id>
</oscope_start_msg>
```

Once the start packet is captured in block 1000, the central control logic 502 captures the data packet sequence for channel 1 in block 1001, channel 2 in block 1002, channel 3 in block 1003, and so on. The final packet transferred may be a capture stop packet 1004.

In one embodiment the personal control logic 602 on the user device 200 creates the data packet 912 and communicates the data packet 912 to the central computing device 109. As an example, the user device 202 may be a mobile device as described that does not communicate via the network device 202. The personal control logic 602 may be configured to transmit the data packet 912 to the central computing device 109 solicited or unsolicited, i.e., the central computing device 109 requests the data packet 912 or the user device 200 automatically transmits the data packet 912 to the central computing device 109. A use of device management protocol is described in U.S. patent application Ser. No. 11/972,275, entitled Wireless Sensor Network Data management System and Method (the '275 application) and U.S. patent application Ser. No. 12/686,342, entitled Human Health Monitoring Systems and Methods (the '342 application), both of which are incorporated herein by reference in their entirety.

The central control logic 502 may store the received RDCR as raw history data 599 in memory 502. Note that data communication techniques, such as HTTP-based web services, may be used to ensure reliable transmission of the data packets 912, even in the event it must be segmented into smaller packets for transmission over the network. These techniques are also used to resolve retransmission policies, out of sequence arrivals, and duplicate transmissions.

As the central control logic 502 receives the data packets 912, the central control logic 502 stores data indicative of the received data packets 912 in real-time in memory 501 in the raw history data 599. When a new RDCR is received by the central control logic 502, the central control logic 502 may assign a unique identifier, e.g., a randomly-generated number, for the record. The data packets 912 may also contain the user identifier and device identifier making it possible for the central control logic 502 to associate the data packet 912 with a particular user and a particular device. In addition, the central control logic 502 may also associate other data with the data packet 912. For example users can later apply various annotative tags for further qualifying the nature of the contained record (e.g., "real fall", "normal motion", "suspect fall", "getting into bed").

Once the data packet 912 is successfully stored as the raw history data 599, it is accessible for review by company scientists, researchers, or engineers tasked with inspecting and improving event detection methods. To facilitate easy access, the central control logic 502 may display an interface (not shown) where users can specify records of interest (by providing timestamp, the global RDCR record identifier, or supplied search terms) and then download the record to a machine readable file format. By way of example, one such file format may be an ASCII text file organized as a comma separated values (CSV) file format. Such a file could also be used easily by analytical research tools such as Mathworks® Matlab™, Microsoft® Excel™ or other analysis package. In addition, this makes it possible to graphically plot each channel from the RDCR on a human readable chart where the X-axis may represents time or sample sequence number and the Y-axis represents the magnitude of the collected sample.

The raw history data captured by the user device 200 and transmitted to the central computing device 109 may be used in a number of ways. In this regard, a caregiver or responder, e.g., a user of the central computing device 109, may be used the raw data to determine conditions that lead to an event. For example, one may be able to determine if a physiological change in the user 102 (FIG. 1), e.g., change in body temperature or heart rate, led to the event, e.g., a fall.

Additionally, the raw history data 599 may be used by researchers and developers to hone the system 100 and create better fall detection methods, for example, or other event detection methods. The raw history data 599 may be used to analyze normal motion patters of a particular user and such analysis may be used to determine a custom algorithm for the user of the user device 200. For example, a particular user 102 of the user device 200 may periodically experience the same physiological changes prior to an event, e.g., the user's heart rate may speed up or slow down prior to the user 102 experiencing unconsciousness. The user's device 200 (and/or the central computing device 109) may be custom configured to detect the user's behavior patterns (or physiological patterns) and in effect predict an imminent event, e.g., a fall.

By way of example, analysis techniques may include inspection of frequency domain characteristics, time domain characteristics, signal processing and filtering techniques, identifying maximum accelerations, integration of said signals, extracted intermediary parameters such as estimated energy expenditure, static acceleration due to gravitational pull, user orientation, and even fractional free fall episodes (where measured gravitational pull is below 1G), etc. Fall detection techniques are described in U.S. patent application Ser. No. 12/192,855 (the '855 application), entitled Wearable Health Monitoring Device and Methods for Fall Detection, which is incorporated herein by reference in its entirety.

In addition to the detailed analysis on individual raw history data 599, scientists and engineers may use the raw history data 599 in aggregate to test a new method on a laboratory computer (not shown) before it is committed to a user's device 200. In one embodiment, the raw history data 599 may be annotated and stored as user data 507. If the raw history data 599 is annotated with either "real fall" or "normal motion" identifiers, a developer may create laboratory test programs that process the user data 507 that contains the raw history data 599 (and annotations) or a subset of the user data 507 with a new proposed algorithm. In this regard, the user data 507 may comprise raw history data 599 with annotations in addition to the variety of other data collected per user, which is indicative of thousands of users physiological characteristics and corresponding behavior patters during performance of a variety of activities, potentially over the course of years. Such user data 507 may be tested programmatically in a laboratory without the need to conduct user empirical testing. Further, the present invention enables RDCRs to be tagged, subdivided, and categorized so that during research particular aspects or types of fall behavior can be improved upon to help fall detection in general.

If a new method is created (especially one customized for a particular user), the software and/or firmware can be tested and transmitted to the user device 200 for execution by processing unit 603. In particular, the software and/or firmware embodying the new method may be transmitted remotely, on an individual basis, across a subset of users, or all devices in the system 100.

The raw history data 599 may also be used to improve customer satisfaction. In this regard, a company representatives may be able to identify dissatisfied customers (those that may be experiencing performance issues with the fall detection capability), and then to obtain raw history data 599 from the user's device 200 during the period of time in which the user 102 was experiencing problems. Company scientists/engineers may analyze the raw history data 599 and determine opportunities for enhancement, implement new software and/or hardware, and test the effectiveness of the new software and/or hardware and/or firmware against the raw history data 599 and/or user data 507 to ensure that the new software and/or hardware and/or firmware works properly.

As described hereinabove, raw history data 599 (or the raw history data 698 on the user device 200) may be used to determine severity of events and/or program sensitivity to events on the user device 200. In this regard, human motion is complex and measured signals can vary greatly due to body sizes, age of the individual, degrees of physical activity, and even individual behavior patterns. In one embodiment, the system 100 (FIG. 1) may incorporate configuration settings (e.g., in the control data 612 in the user device 200) to enable individual adjustment of the software, firmware, and/or hardware after deployment to account for such variations.

In one embodiment, the system 100 may customize event detection methods (e.g., fall detection) per user. For example, the system 100 may be customized to define severity levels and categorize each fall (or detected motion event) into a defined severity category. In this regard, the higher the severity level, the more likely the user will incur injury and the greater the extent of the injury may be. In turn, each parameter used by an employed fall method in the software, firmware, and/or hardware (such as those described in '855 application) may include tiers of thresholds which are associated with the varying degrees of fall severity.

One embodiment may use a method as described in the '855 application where the event detection method relies upon N distinct parameters numbered $Parameter_1$, $Parameter_2, \ldots, Parameter_N$, where each parameter represents a processed signal comprised of discrete samples. Each Parameter includes a threshold for determining if a particular event has occurred, i.e., a parameter has been "triggered." If a parameter is said to have been "triggered," this indicates that the motion pattern detected satisfies the threshold for that particular parameter within a given time constraint. For example, the software, firmware, and/or hardware has a positive output (indicating an event, e.g., a fall, has occurred), when at least M of N parameters trigger co-temporally within a defined time window, and where $1 \leq M \leq N$.

For example, $Parameter_1$ may include a threshold of a specified magnitude $X_1$ and $Parameter_2$ a threshold of magnitude $X_2$ and so forth. In one embodiment, the system 100 associates with each parameter's threshold a severity level. Consequently, $Parameter_1$ will include thresholds $X_{1,1}$, $X_{1,2}$, $X_{1,3}, \ldots, X_{1,K}$ (where K denotes the number of severity levels and each threshold $X_{1,j}$ corresponds to $Parameter_1$ severity level j. In the case where an increasing magnitude of a parameter signifies increasing severity, then $X_{1,1} \leq X_{1,2} \leq X_{1,3} \leq \ldots \leq X_{1,K}$, but the disclosure is in no way limited by this convention.

Thus, the system 100 may not only detect an event, e.g., a fall, but also indicate the severity level of the event. Consequently, a scenario where N parameters are used and N−1 of the parameters satisfy severity level of 3, and the remaining parameter has a severity level of 2, then event would be considered severity level of 2. It is also worth noting that this categorization technique is not limited by this disclosure and is only reference as example. Other examples of event severity categorization may include using the parameter with highest severity, by requiring a specified fraction of parameters (e.g., highest categorization of at least 50% of said parameters), or possibly a weighted function where each parameter carries a unique weight in determination.

In one embodiment, the system 100 comprises a programmable event sensitivity level on a per-user basis. In this regard, the event sensitivity level is a threshold used to determine if an event has occurred and is associated with a specific severity level. For example, each user device 200 can be programmed with default sensitivity levels, and the personal control logic 602 or the central control logic 502 may modify the programmed sensitivity levels based upon new information, e.g., a change in the user's physical condition. When the personal control logic 602 detects and event, the personal control logic 602 is configured to assign a maximum detected severity level in accordance with a severity categorization technique described above. The personal control logic 602 compares the severity level of the detected event to the programmed sensitivity level. If the personal control logic 602 determines that the detected event is not of severity level equal or greater to the programmed sensitivity level, then the detected event is not deemed sufficiently severe. Subsequently, the personal control logic 602 may use this determination for subsequent events to determine whether a detected event is suppressed, reported, or reported in a manner that signifies a non-emergency event. Thus, if a user 102 is experiencing multiple false reports of events (e.g., falls) from performing normal activities, the personal control logic 602 can adjust the sensitivity threshold for optimal performance for a given user and potentially suppress false positives caused by normal activity, but still able to detect real falls from higher severity.

In one embodiment, the central control logic 502 may remotely adjust control data 507 on the user device 200 thereby adjusting a configuration parameter governing sensitivity levels for an event. In this regard, the control data 612 may be modified dynamically so that the personal control logic 602 ignores detected events below a specified severity level. This remote provisioning can be changed by a member of a customer support team, or potentially through a user interface exposed to the user or caregiver. One such embodiment of a user interface is described in U.S. patent application Ser. No. 12/686,296, entitled Human Health Monitoring Graphical User Interface Systems and Methods, which is incorporated by reference in its entirety. In one embodiment, the personal control logic 602, based upon previous raw history data 698) may dynamically augment severity levels, store the change in the RAM 697, and transmit a notification to the central computing device 109 acknowledging the new sensitivity level. At any point, the current level can be retrieved from the device 200 by requesting such information using a management command protocol.

In another embodiment, the sensitivity level could also be set using some other means such as a set of dual in-line package (DIP) switches accessible by the user 102, a slide switch (not shown), or through a graphical user interface (GUI) placed directly on the user device 200 (such as an LCD display (not shown) and menu buttons (not shown)).

In another embodiment, the personal control logic 602 may monitor the user's activity and/or behaviors and profile such activities and/or behavior. For example, the first 48 hours of use of the user device 200 could be used to establish a baseline of physical activity for a user 102. Based on the empirically measured baseline, the sensitivity can be assigned accordingly. Because of the unique instrumentation capabilities of the architecture disclosed within, the sensitivity assignment can be developed in straightforward fashion by collecting historical activity averages for a large set of users, then statistically analyzing the activity levels and corresponding fall algorithm performance to establish guidelines for appropriate sensitivity levels.

In one embodiment, the device 200 can suppress particular events based upon monitored data. In this regard, regardless of a programmed sensitivity level, data indicative of an event can be transmitted to the central computing device 109 and annotate the event with the maximum measured severity. The central control logic 502 may compare the reported event severity level with a configured sensitivity record on behalf of each user. If the event is of severity such that it should be suppressed, the central control logic 502 can suppress notifications and/or Call Center emergency response protocols. Similarly, if it is of sufficient severity that it requires action, then normal response protocol can be followed.

In one embodiment, the system 100 can determine whether a change in severity levels would be beneficial. The system described resembles a system as described in U.S. patent application Ser. No. 12/686,342 where all fall detection devices report fall events to a personal monitoring computing device where it is stored in a database. The database allows for data to be collected for all events (e.g., falls) across all users of the system as well as the capability to look at all events (or a subset of events) for a given user. From this data, an individual may employ statistics to provide information about any patterns in the behavior of a given user, such as frequent falls of a given severity level. The central control logic 502 may then transmit notifications for a caregiver or a responder to use to evaluate whether to change the sensitivity threshold or to change automatically based on pre-set conditions. Additionally, a user or caregiver may request adjustment (or make adjustments through a GUI) based on their own experience and observation.

During the process where user movements are being evaluated to detect falls as described in the '855 patent, parameters used to determine a fall may be retained in system memory in data structures (i.e., a list) and the personal control logic 602 may use the parameter data to evaluate if an event, e.g., a fall, has occurred. In one embodiment, the personal control logic 602 may update fall parameters based upon discrete data obtained from the sensors. The personal control logic 602 uses the data (as described in the '855 application) to determine if a fall has occurred, for example. The personal control logic 602 then saves this data in memory 501 has user data 119 and associated with the reported fall event by an associated timestamp or a unique fall identifier. The personal control logic 602 may then transmit the parameters to a central computing device 109. One such method is described in the '342 application where they are stored with their associated fall identifier and timestamp for future reference. The user device 200 may transmit the parameters in a fall notification message sent to the central computing device 109, and the central control logic 502 associates the new parameters for immediate access. In one embodiment, the user device 200 may deliver the new parameters separately In addition to verification, retrieval of fall parameters can yield insight in refining the thresholds used in a given fall algorithm such as described in the '855 application. By gathering statistics about fall severity and analyzing individual parameter performance in that context can lead to data-driven improvement of individual parameters. This can also be used to develop and improve user sensitivity level assignment.

Furthermore, the entire collection of event parameter data 598 and raw history data 599 may be used to refine thresholds used to identify severity of an event, e.g., a fall. In this regard, one may cross-reference an outcome of a detected event, such as for example, the degree of injury sustained, or user reported severity, with the event parameter data 598 and the raw history data 599. In response to the comparison, the severity levels of the event parameter data 695 or raw history data 698 may be adjusted manually or automatically as described hereinabove. Such a comparison may further be used to identify false event reporting. In this regard, over time patterns can develop that correlate certain event parameter data 695 with particular activities of daily living. These patterns can lead scientists and engineers to refine the methods employed by the personal control logic 602 (FIG. 5) to reject false positives for specific normal motion patterns.

In one embodiment, during a process where user movements are being evaluated to detect falls as described in the '855 application state variables are used to make a fall determination. Such state variables are hereinafter referred to as "fall metadata." The fall metadata is data indicative of calculated and measured values that are used by the system 100 (including the personal control logic 602 and the central control logic 502) is retained in memory in data structures (i.e., a list) and used to evaluate if a fall occurred. The fall metadata is updated each time the personal control logic 602 performs a fall detection algorithm to determine if a fall has occurred.

When the personal control logic 602 determines that the fall metadata indicates a fall has occurred, the personal control logic 602 stores the fall metadata as time-stamped data 699 in the user data 110 and associated with the event data, i.e., the motion data 614 or the physiological data 611. Further, the personal control logic 602 associates a timestamp or a unique fall identifier with the metadata.

The personal control logic 602 then transmits the fall metadata, e.g., the time-stamped data 699, to the central computing device 109. Such process including transmission is described in the '342 application. The time-stamped data 699 and any other relevant data, which may include the raw history data 698, is stored as event metadata 597 with an associated event identifier and timestamp for future reference. These corresponding event parameter data 695 may also be sent to the central computing device 109 as part of the same fall notification message to ensure proper association and immediate access to event parameter data 695, user data 507, or raw history data 599, or they may be delivered separately should combining the additional data with the fall event not be practical or possible.

Post-mortem retrieval of fall parameters empowers the development process and aids ongoing refinement of fall detection algorithms. A device that is malfunctioning may be using or reporting corrupted fall parameters or measurements, leading to erroneous fall events. When combined with raw data capture support, it serves as a verification mechanism for proper operation of the device and fall algorithm by checking that the fall parameters calculated by the device for a given event match those calculated from the raw capture data from the same event.

In addition to verification, retrieval of fall parameters can yield insight in refining the thresholds used in a given fall algorithm such as described in the '855 application. By gathering statistics about fall severity and analyzing individual parameter performance in that context can lead to data-driven improvement of individual parameters. This can also be used to develop and improve user sensitivity level assignment algorithms as described herein.

Furthermore, the entire collection of stored event parameter data 598 and raw history data 599 can be used to refine the threshold tiers used to identify the severity of a fall. In this regard, one may cross-reference the outcome of a fall event, such as the degree of injury sustained, or user reported severity, with the event parameter data 598 or raw history data 599 collected to adjust configurable sensitivity levels, as described hereinabove. Scientists can use the data to properly match the injury level of a fall with a detected fall severity of level. False fall rejection can also be improved by cross-referencing collected event parameter data 598 and the raw history data 599 with event outcomes as well. Over time, patterns can develop that correlate certain parameter levels with particular activities of daily living. These patterns can lead scientists and engineers to refine the algorithm to reject false positives for specific normal motion patterns.

Figure 7:
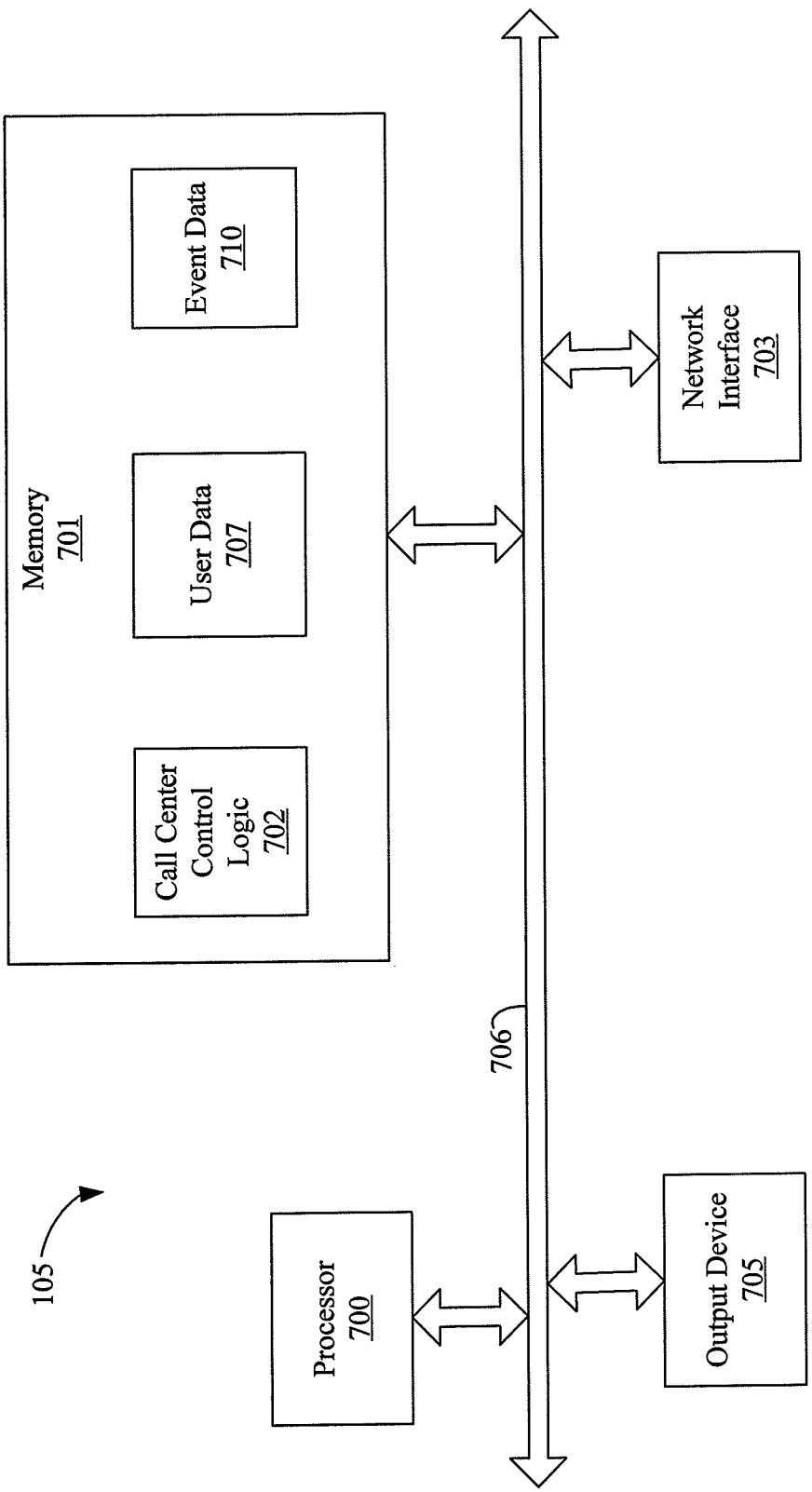
FIG. 7 is a block diagram of an exemplary call center system such as is depicted in FIG. 1.

FIG. 7 depicts an exemplary embodiment of the call center system 105. The call center system 105 comprises call center control logic 702 for generally controlling the operation and functionality of the call center system 105. In the exemplary embodiment shown by FIG. 7, call center control logic 702 is implemented in software and stored in memory 701. In other embodiments, the call center control logic 702 may be implemented in firmware, hardware, or any combination of software, firmware, and/or hardware.

The call center system 105 further comprises user data 707 stored in memory 701. The user data 707 data related to the user 102 that is received from the central computing device 109, including any data determined by the central computing device 109 based upon the user data 110 received from the user device 200.

The exemplary embodiment of the call center system 105 depicted by FIG. 7 includes a processor 700, which comprises processing hardware for executing instructions stored in memory 801. The processor 700 communicates to and drives the other elements within the call center system 105 via a local interface 706, which can include at least one bus.

Furthermore, the call center system 105 comprises a network interface 703. The network interface 703 may be any type of communication device that communicatively couples the call center system 105 with the network 101 (FIG. 1) and the call center system 105 and the remote access a server 107.

In addition, the call center system 105 comprises an output device 705. The output device 705 may be any type of device known in the art or future-developed that provides data to a user (or caregiver) using the call center system 105. As a mere example, the output device 705 may be a liquid crystal display (LCD).

Furthermore, the call center system 105 comprises an input device 710. The input device 710 may be, for example, a keyboard.

In one embodiment, the call center system 105 is available 24/7 to assist users in response to an event. In this regard, the call center control logic 702 receives data indicative of an event from the central computing device 109. The call center control logic 702 stores the received event data as event data 710. The event data 710 may comprise data indicative of a type of alert, the location of the user, and/or the time the event occurred. In response, the call center control logic 702 automatically attempts to establish contact with the user 102 (FIG. 1) via the telephone network 106 directly calling the user device 200 (FIG. 2) or a user of the call center system 105 manually establishing, e.g., calling, the user device 200. If the user 102 responds to the attempted contact and requests help or the user device 200 automatically answers but no contact is made with the user 102, the user of the call center system 105 may dispatch necessary emergency responders to the user 102 based upon the location information contained in the event data 710. Notably, the personal control logic 602 is configured to automatically answer such a call from the call center system 105 in the event that the user 102 is unable to take action to respond to the call.

In one embodiment, the user device 200 (FIG. 2) may initiate a call to the call center system 105 once an event has occurred, for example if the user 102 is still capable of taking action or a caregiver (not shown) is with the user 102 when the event occurs. In such an embodiment, the call center control logic 702 dynamically bind, e.g., by associating data indicative of the telephone number calling obtained from a caller identification (caller ID) system with data indicative of the event that has occurred. In this regard, the event data 710 may comprise an identifier (e.g., the mobile phone number of the device 200) that the call center control logic 702 may used to associate the event data 710.

In one embodiment, the user device 200 establishes a modem call directly with the call center system 105. When the call center system 105 answers such a call, event data 710 and/or user data 707 may be transmitted after connection. When such a call is answered, the call center control logic 702 connects the call to a call center system user and switches the call to voice mode thereby establishing a voice call between the user 102 and the user and/or caregiver at the call center system 105. Such binding of the event data 710 and the incoming call from the user device 200 may further be associated with event data 710 and user data 707 obtained from the central computing device 109.

The user device 200 may efficiently deliver the user data 110 to the central computing device 109. In one embodiment, the user device 200 may employ a less reliable transport mechanism and a best-effort transmission policy such as provided by the User Datagram Protocol (UDP). Best-effort delivery, like that used in UDP transmissions, allows the transmissions to be connectionless. In one embodiment, data transmitted is in the form of a binary data object.

If UDP is employed, datagrams (as defined by the UDP) sent by the user device 200 may comprise a sequence number so that redundant transmissions can be identified, a timestamp to indicate when in time these measurements were taken, a type field to identify the type of measurements that are reported assuming the type reported is not always the same, and control fields to enable a simple acknowledgement system to ensure data is properly delivered. Other data that may be sent with a datagram containing the user data 110 is described with reference to the '342 application.

In one embodiment, the central computing device 109 poles a port (not shown) on the central computing device 109. If a datagram is received, the central control logic 502 continues to receive and store subsequent datagrams until the last datagram (in the sequence) is received. In this regard, the central control logic 502 will keep a running table to the last sequence number received from each user device 200 from which central control logic 502 has received messages (with timeouts to remove an entry after a certain threshold of time has expired without activity). Thus, the central control logic 502 can ignore duplicates receipts of user data 110. Once this has occurred, the central control logic 502 transmits an acknowledgement to the user device 200.

In one embodiment, the central control logic 502 may request a management operation for the user device 200 (e.g., firmware upgrade, remote provisioning, reset of device). In such an embodiment, when user data 110 is reported to the central control logic 502, the central control logic 502 may transmit data in the acknowledgement that indicates that a management operation is pending. For example, the central control logic 502 may set a flag (toggle a bit) in the acknowledgement sent to the user device 200 to indicate the management operation is pending. In such an embodiment, the central control logic 502 waits until it receives a counter acknowledgement from the user device 200 and may resend periodically if no acknowledgement is received from the user device 200. When the user device 200 receives such a flagged acknowledgement, transmits an acknowledgement to the central control logic 502 and transmit an additional message for instruction from the central control logic 502. Because management operations are infrequent and subsequently will not have a significant impact on overall data usage, the connection established for instruction may or may not use a different protocol, such as a REST POST interface described in the '335 application. The central control logic 502 and the user device personal control logic 602 may comprise timeout logic to prevent deadlock should communications fail during transmission.

In another embodiment, the central control logic 502 transmits an acknowledgement to the user device 200 after each user data transmission is received that contains the sequence number of the last user data 110 received. If the user device 200 does not receive the acknowledgement—in the event that the acknowledgement is either lost in transit or that the original packet never arrived at the server—it will retransmit the original user data 110 according to a particular waiting period.

In one embodiment, a Virtual Private Network (VPN) can be erected between the network 108 and the central computing device 109 in order to protect user data 110 traveling through network 101. In one embodiment, IPSec or another protocol may be may be used to establish the VPN and encrypt the data. With this method, data is still securely transmitted end-to-end, but the additional overhead of this VPN tunnel is not borne by the expensive wireless segment of the system 100 and the user data 110 is still protected.

In one embodiment of the system 100, the central computing device 109 uses the location data (e.g., GPS coordinates) contained in the user data 507 to identify a proper Public Service Access Point (PSAP) for the user 102 who is in need of emergency help. The PSAP is a 10-digit equivalent of 9-1-1 access and can be assigned statically into the user device 200. In addition, the personal monitoring computer device 109 may search a list of identifiers and associated PSAP numbers based upon the location of the user 102 as identified in the user data 110 received by the central computing device 109. In one embodiment, the central control logic 502 may determine a street address near the user 102 and perform an indexed lookup for emergency service based on street information.

In another embodiment of the system 100, the central computing device 109 transmits location data and/or nearby street information from call center system 105. The call center system 105 may automatically determine an appropriate PSAP or a caregiver may manually find an appropriate PSAP.

In another embodiment, the user device 200 establishes not only 2-way communication, but 3-way communication as well with the call center system 105. The call center system 105 contacts the user device 200 to determine if assistance is needed. If help is desired, the Call Center establishes a 3-way call such that the user device 200 calls emergency services using e911. By utilizing the e911 system (not shown), the central computing device 109 and the call center system 105 would never need to resolve PSAP.

In another embodiment, the system 100 provides information that a caregiver can use to locate a user 102 other than the GPS coordinates as provided by the user device 200. For example, the call center control logic 702 can display a map centered directly on the last known location (provided by GPS if outdoors or cellular triangulation to assist the GPS if indoors where GPS alone may not function) of the user 102. On such a map, the control logic 702 may highlight a nearby street or intersection or apply a circle around the location of the user 102. In one embodiment, the displayed map can overlay GPS coordinates of the user 102 with street level pictures showing what the area near the user 102 looks like and marking nearby buildings.

In one embodiment, the user data 110 received from the user device 200 may be used to calculate an elevation location of the user 102, e.g., what floor a user may be located on in a building. In this regard, the barometer 621 obtains and stores data indicative of the pressure that the personal control logic 602 or the central control logic 502 may use to determine elevation location. The elevation location information, stored as location data 623, is transmitted to the central computing device 109.

The elevation location information contained in the user data 110 may be used to determine the user's elevation above sea level. The central control logic 502 can use the elevation information, i.e., the barometric pressure at the time the user data 110 was obtained, and translate the user data 110 containing the barometric pressure into feet to determine where (i.e., what floor) a user is located on in a building.

In addition, the central control logic 502 may use the longitude and latitude measurements to access a service of a global elevation database. The central control logic 502 may use the elevation data retrieved to calculate a difference between the measured elevation and the retrieved elevation to obtain the user's height above the "street level," i.e., the height above sea level for the location represented by the latitude and longitude data identifying the user's location. The difference between the height above sea level at the particular location and the user's height above sea level is transmitted to emergency personnel, either through voice or electronically, so the emergency personnel can locate the user 102. For example, the user may be 80 feet above street level, which may indicate that the user is on the $8^{th}$ floor of a building or in a treetop.

Because this information is provided verbally to emergency service responders, it will be up to the responders to interpret the details and use judgment on which floor the user may actually be located. But providing this information can save precious minutes by narrowing the search to a starting floor. In very large structures, this may mean the difference between life and death if responders cannot locate the user's floor in the structure.

Barometers are subject to a number of variations, such as temperature. In order to calculate the absolute height above sea level, the present disclosure does not necessarily require problematic, error-prone, and expensive factory calibration techniques and devices. The user device 200 circumvents using such techniques and devices by determining a baseline elevation, referred to as a "street level" elevation, and measuring the changes in elevation (i.e., height of user 102) in relation to the "street level" elevation. Thus, a caregiver can provide more definitive information to a responder about a user's location without reference to a global elevation database. In such an embodiment, the user device personal control logic 602 may query the accelerometer and use the result to calibrate street level as a point of reference. In this embodiment, the user device personal control logic 602 compares readings from the accelerometer 606 and the barometer 621 and compares those readings to threshold values, i.e., values that have been determined to indicate motion of the user, in order to determine when the user is in motion. If the user's location is changing, the user device personal control logic 602 samples the barometer to obtain a set of "street level" data. The user device personal control logic 602 may average accelerometer and the barometer data over a time interval. Thresholds for "in transit" are set so that they will not pick up movement in typical structures. For example walking around a parking garage is not sufficient movement to trigger "in transit." As an example, "in transit" could mean travelling more than a half mile in one hour. In addition, "in transit" would be set so that it is unlikely or impossible to be "in transit" while ascending or descending stairs or an elevator. In this fashion, the user device personal control logic 602 allows the pressure recorded at an actual event time to be compared to the pressure at last known street level calibration. The difference represents an elevation change representative of the user's approximate height above street level and can be conveyed to responders as described above. In such an embodiment, the barometer 621 need not be very accurate because we have no interest in absolute elevation above sea level. Instead, the personal control logic 602 determines changes in elevation (and not absolute accuracy).

In one embodiment, the personal control logic 602 may use a transportation map and/or database to further refine the "street level" approximation. For example, when the user device 200 determines that the user 102 is "in transit" and is at "street level," the personal control logic 602 may use his/her location and path of movement to determine if the user 102 is on a public transportation system such as an underground train or subway. In such a case, the user's calibrated street level is augmented with this data to determine actual street level by knowing the user was 40 feet underground during the last calibration. This adjustment could happen in real-time by communicating with the central control logic 502 or the user device personal control logic 602 may adjust resolution time by delivering (either with the event or periodically) so that the central control logic 502 can determine if the last calibrated location was in effect "street level" or if additional adjustment is required.

Figure 11:
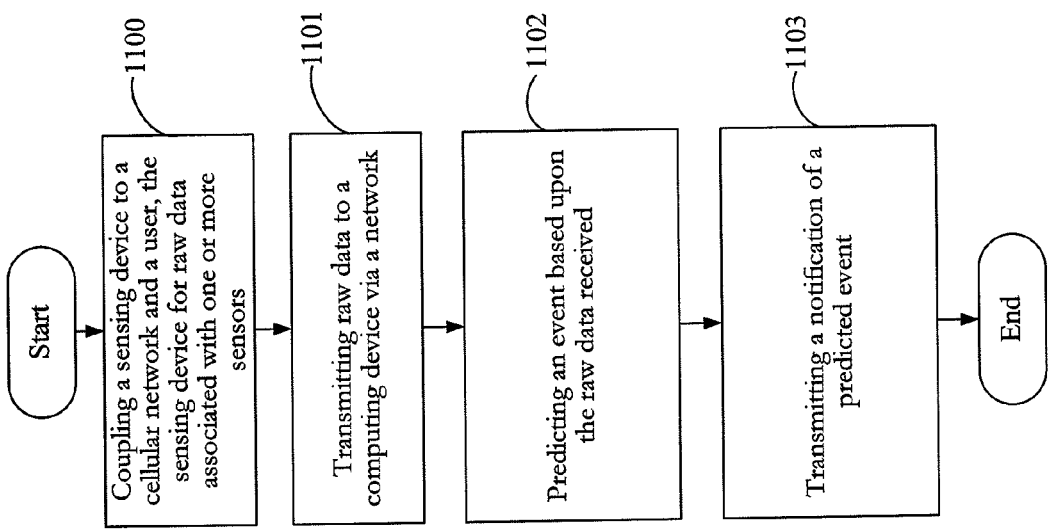
FIG. 11 is a flowchart of exemplary architecture and functionality of the system such as is depicted in FIG. 1.

FIG. 11 is a flowchart depicting exemplary architecture and functionality of the system 100.

In step 1100, a sensing device, i.e., user device 200 (FIG. 2), is coupled to a network 108 (FIG. 1) and the sensing device collects raw data from the sensing device related to the user 102 (FIG. 1). In step 1101, the sensing device transmits raw history data 599 (FIG. 6) to a computing device 109 (FIG. 1) via the network 108.

In step 1102, the central control logic 502 (FIG. 5) determines a whether an event has occurred or is likely to occur based upon the raw history data 599. Further, with reference to step 1103, the central control logic 502 transmits data indicative of the predicted event, for example to a caregiver or the call center system 105.

What is claimed is:

1. A personal monitoring system, comprising:
    a network;
    a sensing device comprising a network interface for coupling the sensing device to the network, the sensing device coupled to a user for sensing raw data at a discrete time related to the user; and
    logic configured to associate a timestamp with the raw data at the discrete time and store the raw data as raw history data indicative of a plurality of raw data from discrete times and determine, based upon the raw history data, whether an event has occurred, wherein the logic is further configured to predict an upcoming event based upon a plurality of sets of raw data at discrete times.

2. The personal monitoring system of claim 1, wherein the logic is further configured to determine a severity level of the event.

3. The personal monitoring system of claim 1, wherein the logic stores the raw data based upon a triggering event.

4. The personal monitoring system of claim 3, wherein the triggering event is a detected fall by the user.

5. The personal monitoring system of claim 4, wherein the triggering event is based upon a manual input.

6. The personal monitoring system of claim 1, wherein the logic is further configured to disable storing raw data based upon an input.

7. The personal monitoring system of claim 1, wherein the logic is further configured to activate storing raw data based upon an input.

8. The personal monitoring system of claim 1, the logic is further configured to store a plurality of sets of raw data sensed at discrete times over a period of time in nonvolatile memory.

9. The personal monitoring system of claim 8, wherein the logic is further configured to create a data structure containing the plurality of sets of raw data in a data structure.

10. The personal monitoring system of claim 9, wherein the data a structure comprises a data indicative of a timestamp, a device identifier, a customer identifier, a sequence identifier, and an array of data indicative of a plurality of samples over time of the sensing device.

11. The personal monitoring system of claim 1, wherein the logic is further configured to test an event detection method using a plurality of sets of raw data at discrete times.

12. The personal monitoring system of claim 1, wherein the logic is further configured to compare raw data from the sensing device with a threshold value to determine whether the event has occurred.

13. The personal monitoring system of claim 1, wherein the logic is further configured to compare raw data from the sensing device with a threshold value to determine a severity level associated with the event.

14. The personal monitoring system of claim 1, wherein the logic is further configured to adjust a threshold corresponding to the event.

15. The personal monitoring system of claim 14, wherein the logic is further configured to adjust the threshold correspond to the event based upon raw data indicative of a previous event.

16. A personal monitoring method, comprising:
    coupling a sensing device to a network, the sensing device coupled to a user;
    sensing raw data at a discrete time related to the user;
    associating a timestamp with the raw data at the discrete time;
    storing the raw data as raw history data indicative of a plurality of raw data from discrete times;
    determining, based upon the raw history data, whether an event has occurred; and
    predicting an upcoming event based upon a plurality of sets of raw data at discrete times.

17. The personal monitoring method of claim 16, further comprising determining a severity level of the event.

18. The personal monitoring method of claim 16, further comprising storing the raw data based upon a triggering event.

19. The personal monitoring method of claim 18, wherein the triggering event is a detected fall by the user.

20. The personal monitoring method of claim 18, wherein the triggering event is based upon a manual input.

21. The personal monitoring method of claim 16, wherein further comprising disabling storing raw data based upon an input.

22. The personal monitoring method of claim 16, further comprising activating storing raw data based upon an input.

23. The personal monitoring method of claim 16, further comprising storing a plurality of sets of raw data sensed at discrete times over a period of time in nonvolatile memory.

24. The personal monitoring method of claim 23, further comprising creating a data structure containing the plurality of sets of raw data in a data structure.

25. The personal monitoring method of claim 24, wherein the data a structure comprises a data indicative of a timestamp, a device identifier, a customer identifier, a sequence identifier, and an array of data indicative of a plurality of samples over time of the sensing device.

26. The personal monitoring method of claim 16, further comprising testing an event detection method using a plurality of sets of raw data at discrete times.

27. The personal monitoring method of claim 16, further comprising comparing raw data from the sensing device with a threshold value to determine whether the event has occurred.

28. The personal monitoring method of claim 16, further comprising comparing raw data from the sensing device with a threshold value to determine a severity level associated with the event.

29. The personal monitoring method of claim 16, further comprising adjusting a threshold corresponding to the event.

30. The personal monitoring method of claim 29, further comprising adjusting the threshold correspond to the event based upon raw data indicative of a previous event.

31. A personal monitoring system, comprising:
    a network;
    a sensing device comprising a network interface for coupling the sensing device to the network, the sensing device coupled to a user for sensing raw data at a discrete time related to the user; and
    logic configured to associate a timestamp with the raw data at the discrete time and store the raw data as raw history data indicative of a plurality of raw data from discrete times and determine, based upon the raw history data, whether an event has occurred, wherein the logic is further configured to test an event detection method using a plurality of sets of raw data at discrete times.

32. A personal monitoring system, comprising:
    a network;
    a sensing device comprising a network interface for coupling the sensing device to the network, the sensing device coupled to a user for sensing raw data at a discrete time related to the user; and
    logic configured to associate a timestamp with the raw data at the discrete time and store the raw data as raw history data indicative of a plurality of raw data from discrete times and determine, based upon the raw history data, whether an event has occurred, wherein the logic is further configured to compare raw data from the sensing device with a threshold value to determine whether the event has occurred.

33. A personal monitoring system, comprising:
    a network;
    a sensing device comprising a network interface for coupling the sensing device to the network, the sensing device coupled to a user for sensing raw data at a discrete time related to the user; and
    logic configured to associate a timestamp with the raw data at the discrete time and store the raw data as raw history data indicative of a plurality of raw data from discrete times and determine, based upon the raw history data, whether an event has occurred, wherein the logic is further configured to compare raw data from the sensing device with a threshold value to determine whether the event has occurred.

34. A personal monitoring system, comprising:
    a network;
    a sensing device comprising a network interface for coupling the sensing device to the network, the sensing device coupled to a user for sensing raw data at a discrete time related to the user; and logic configured to associate a timestamp with the raw data at the discrete time and store the raw data as raw history data indicative of a plurality of raw data from discrete times and determine, based upon the raw history data, whether an event has occurred, wherein the logic is further configured to compare raw data from the sensing device with a threshold value to determine a severity level associated with the event.

35. A personal monitoring system, comprising:
a network;
a sensing device comprising a network interface for coupling the sensing device to the network, the sensing device coupled to a user for sensing raw data at a discrete time related to the user; and
logic configured to associate a timestamp with the raw data at the discrete time and store the raw data as raw history data indicative of a plurality of raw data from discrete times and determine, based upon the raw history data, whether an event has occurred, wherein the logic is further configured to adjust a threshold corresponding to the event.

36. The personal monitoring system of claim 35, wherein the logic is further configured to adjust the threshold correspond to the event based upon raw data indicative of a previous event.

37. A personal monitoring method, comprising:
coupling a sensing device to a network, the sensing device coupled to a user;
sensing raw data at a discrete time related to the user;
associating a timestamp with the raw data at the discrete time;
storing the raw data as raw history data indicative of a plurality of raw data from discrete times;
determining, based upon the raw history data, whether an event has occurred; and
testing an event detection method using a plurality of sets of raw data at discrete times.

38. A personal monitoring method, comprising:
coupling a sensing device to a network, the sensing device coupled to a user;
sensing raw data at a discrete time related to the user;
associating a timestamp with the raw data at the discrete time;
storing the raw data as raw history data indicative of a plurality of raw data from discrete times;
determining, based upon the raw history data, whether an event has occurred; and
comparing raw data from the sensing device with a threshold value to determine whether the event has occurred.

39. A personal monitoring method, comprising:
coupling s sensing device to a network, the sensing device coupled to a user;
sensing raw data at a discrete time related to the user;
associating a timestamp with the raw data at the discrete time;
storing the raw data as raw history data indicative of a plurality of raw data from discrete times;
determining, based upon the raw history data, whether an event has occurred; and
comparing raw data from the sensing device with a threshold value to determine a severity level associated with the event.

40. A personal monitoring method, comprising:
coupling s sensing device to a network, the sensing device coupled to a user;
sensing raw data at a discrete time related to the user;
associating a timestamp with the raw data at the discrete time;
storing the raw data as raw history data indicative of a plurality of raw data from discrete times;
determining, based upon the raw history data, whether an event has occurred; and
adjusting a threshold corresponding to the event.

41. The personal monitoring method of claim 40, further comprising adjusting the threshold correspond to the event based upon raw data indicative of a previous event.

\* \* \* \* \*